(12) United States Patent
Mehrhof

(10) Patent No.: US 8,597,024 B2
(45) Date of Patent: Dec. 3, 2013

(54) TWO-PART DENTAL IMPLANT

(75) Inventor: Jürgen Mehrhof, Berlin (DE)

(73) Assignee: Mehrof Implant Technologies GmbH, Berlin (DE)

( * ) Notice: Subject to any disclaimer, the term of this patent is extended or adjusted under 35 U.S.C. 154(b) by 0 days.

(21) Appl. No.: 13/421,333

(22) Filed: Mar. 15, 2012

(65) Prior Publication Data

US 2012/0251976 A1  Oct. 4, 2012

Related U.S. Application Data

(63) Continuation of application No. 11/992,084, filed as application No. PCT/EP2006/066378 on Sep. 14, 2006, now Pat. No. 8,202,088.

(30) Foreign Application Priority Data

| Sep. 16, 2005 | (DE) | 20 2005 015 074 U |
| May 9, 2006 | (DE) | 20 2006 007 639 U |
| Jun. 30, 2006 | (DE) | 20 2006 010 431 U |
| Aug. 25, 2006 | (DE) | 10 2006 040 457 |

(51) Int. Cl.
*A61C 8/00* (2006.01)

(52) U.S. Cl.
USPC .......................................................... 433/173

(58) Field of Classification Search
USPC .................................................. 433/172–176
See application file for complete search history.

(56) References Cited

U.S. PATENT DOCUMENTS

| 4,927,363 A | 5/1990 | Schneider et al. |
| 4,943,950 A | 7/1990 | Beasley et al. |
| 4,950,161 A | 8/1990 | Richter |
| 5,425,639 A | 6/1995 | Anders |
| 5,695,335 A | 12/1997 | Haas et al. |
| 5,782,918 A | 7/1998 | Klardie et al. |
| 5,839,898 A * | 11/1998 | Fernandes ..................... 433/173 |

(Continued)

FOREIGN PATENT DOCUMENTS

| DE | 4041378 A1 | 6/1992 |
| DE | 9308090 U1 | 5/1993 |

(Continued)

OTHER PUBLICATIONS

R. Herrmann et al., Implant for Anchoring Dental Devices, Derwent Patent Abstract, DE19828018.

(Continued)

*Primary Examiner* — Eric Rosen
(74) *Attorney, Agent, or Firm* — Price Heneveld LLP

(57) ABSTRACT

A two-part dental implant includes distal and proximal stem portions which in an interconnected condition at least indirectly adjoin each other at a connecting location and have mutually facing surfaces in the region of the connecting location. A sealing body is provided between the mutually facing surfaces of the distal and proximal stem portions. The sealing body has sealing surfaces which face towards the mutually facing surfaces and which in the interconnected condition of the two stem portions bear sealingly against the mutually facing surfaces thereof. In addition, mutually facing abutment surfaces are provided between the distal and proximal stem portions. These mutually facing abutment surfaces bear against each other in the final assembled dental implant and limit the degree of approach of the two mutually facing surfaces of the stem portions between which the sealing body is arranged.

28 Claims, 37 Drawing Sheets

(56) References Cited

U.S. PATENT DOCUMENTS

| | | |
|---|---|---|
| 5,919,043 A | 7/1999 | Weigl |
| 5,947,734 A | 9/1999 | Hanel |
| 6,116,904 A | 9/2000 | Kirsch et al. |
| 6,152,737 A | 11/2000 | Beaty et al. |
| 6,315,563 B1 | 11/2001 | Sager |
| 6,343,930 B1 | 2/2002 | Beaty et al. |
| 2004/0121286 A1 | 6/2004 | Aravena et al. |
| 2005/0087417 A1 | 4/2005 | Shimomura et al. |
| 2005/0186537 A1 | 8/2005 | Gersberg |
| 2007/0059666 A1 | 3/2007 | Zickman et al. |

FOREIGN PATENT DOCUMENTS

| | | |
|---|---|---|
| DE | 19609174 | 9/1996 |
| DE | 19633570 C1 | 1/1998 |
| DE | 19664307 A1 | 5/1998 |
| DE | 19828018 A1 | 12/1999 |
| DE | 10315399 A1 | 9/2004 |
| EP | 0323823 A2 | 12/1988 |
| EP | 0323823 A2 | 7/1989 |
| EP | 0323823 B3 | 7/1989 |
| EP | 0711533 A1 | 10/1995 |
| EP | 0842643 | 5/1998 |
| EP | 1371342 | 12/2003 |
| RU | 1564442 | 5/1990 |
| WO | WO 98/52487 | 11/1998 |
| WO | WO 99/52464 | 10/1999 |
| WO | WO 2004/032786 | 4/2004 |
| WO | WO 2005044133 A1 | 5/2005 |

OTHER PUBLICATIONS

R. Schroeder, Screw-in Jaw Implant for Tooth Inserts and Crowns, Derwent Patent Abstract, DE19646307.

R. Schroeder, Dental Implant, Derwent Patent Abstract, DE10315399.

S. Moisiadis, Metallic Dental Implant in Socket, Derwent Patent Abstract, DE4041378.

* cited by examiner

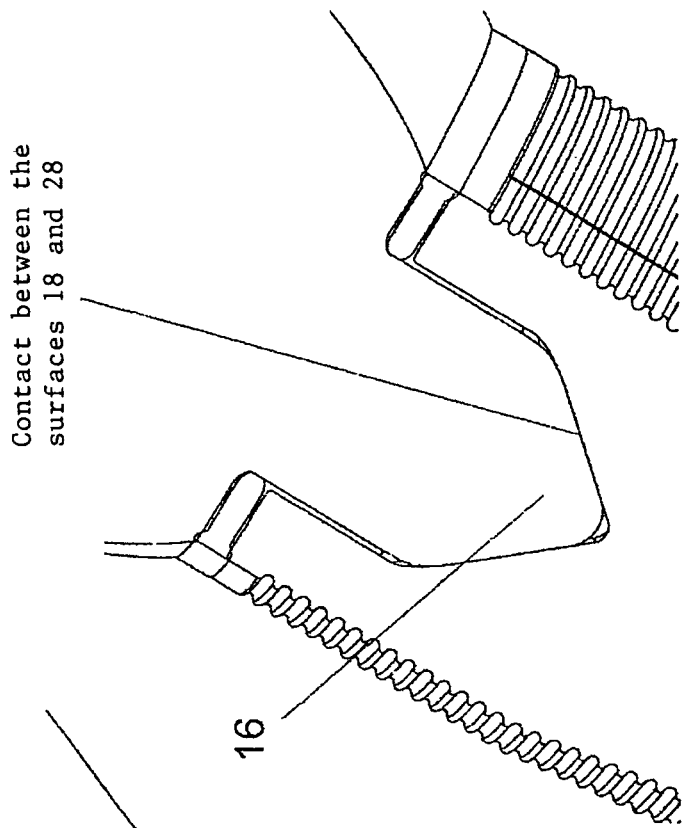
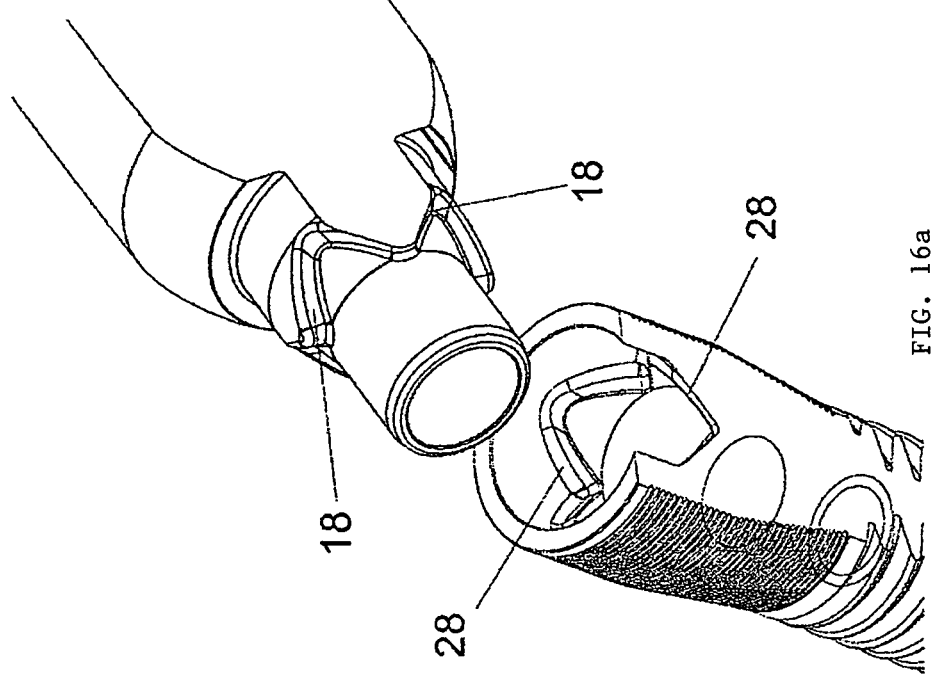

TWO-PART DENTAL IMPLANT

This application is a continuation application of U.S. Ser. No. 11/992,084 filed Jun. 13, 2008, now U.S. Pat. No. 8,202,088 which was the National Stage of International Application No. PCT/EP2006/066378 filed Sep. 14, 2006.

BACKGROUND OF THE INVENTION

1. Technical Field

The invention concerns a two-part dental implant. A distal implant portion is in the form of an artificial tooth root for implantation in a jawbone and a proximal implant portion carries an artificial tooth crown.

The invention concerns in particular the connection between the distal and the proximal implant portions, hereinafter also referred to as the implant-abutment connection and abbreviated to IAC. The proximal end of the distal implant portion and the distal end of the proximal implant portion are of a geometrically mutually matching configuration and adjoin each other in the implanted condition of the stem.

2. Description of the Background Art

Dental implants serve to replace teeth which have been lost. A distinction is drawn in relation to dental implants between one-part and two-part systems. The present invention concerns a two-part system. Two-part systems of that kind have a distal implant portion and a proximal implant portion. The distal implant portion is introduced into the jawbone and there grows to the bone. The proximal implant portion—also referred to as the abutment—protrudes some millimeters into the oral cavity and serves as an artificial tooth stump. In the present case the distal implant portion forms an artificial tooth root while the proximal implant portion forms the above-mentioned artificial tooth stump. The proximal implant portion receives a tooth substitute of the most widely varying forms, for example in the form of a crown, and connects it to the jaw by way of the distal implant portion.

The distal implant portion and the proximal implant portion are usually connected together in the longitudinal direction by a screw pin extending in the longitudinal direction. The geometry of the connecting region between the distal implant portion and the proximal implant portion is such that the connection between the two implant portions is of a force-locking nature or a positively locking nature or both.

The most important demands made on the connection between the distal implant portion and the proximal implant portion are: the connection must be stable as it is subjected to enormous mastication forces. The matching portions must be very precisely worked and may not have any gaps in the assembled state. The tooth structure is to be such that at any time it can be released from the implant and re-connected thereto. The tooth structure is to be such that it can also be replaced by other tooth structures. The two implant portions in the connected state must be rigid and without play and must be prevented from rotating about the longitudinal axis of the implant. That is of particular significance if a plurality of implants have been fitted in a jaw and those individual implants are to receive a complex interconnected construction such as for example a screwed fixed implant bridge. Such an implant construction can be appropriately accurately produced only when the implant portions are exactly prevented from rotating. If a plurality of implant structures are connected directly together, for example in the case of a bridge substructure which generally carries a removable prosthesis, it is possible to dispense with a rotation-preventing configuration. In regard to the demands already listed above, a further demand is made on the bridge structures intended for that use: bridge structures must afford the possibility that a plurality of interconnected tooth structures can then also be fitted on to the implants without any problem and connected thereto when the implant fixings, as usual, are not introduced into the jaw in mutually parallel relationship.

Known two-part dental implants do not satisfy the above-indicated demands to the desired degree. A particular problem in many known two-part implants is the transition between the two implant portions. Known proposals for a solution in that respect, for example as disclosed in EP 0 842 643, U.S. Pat. No. 5,919,043, EP 1 371 342 or U.S. Pat. No. 6,152,737, are not satisfactory.

SUMMARY OF THE INVENTION

The object of the invention is to provide a two-part dental implant which is improved in regard to the aforementioned demands.

According to the invention that object is attained by a two-part dental implant in which provided between the proximal implant portion and the distal implant portion is a seal which is formed by means of a sealing body and which seals off the oppositely disposed surfaces of the proximal and the distal implant portions in such a way that no germs and bacteria can enter.

Preferably the distal and the proximal implant portions have mutually facing abutment surfaces which bear against each other when the tooth implant is in the final fitted condition. The mutually facing abutment surfaces limit the degree of approach of the two mutually facing surfaces of the implant portions, between which the sealing body is arranged, and thus the maximum compression of the sealing body, insofar as the abutment surfaces define a minimum spacing of the two mutually facing surfaces of the implant portions. That ensures that axial forces acting on the implant such as mastication forces are not carried by the sealing body but are transmitted by way of the mutually facing abutment surfaces.

In a preferred variant of the sealing body those sealing surfaces comprise elastic material so that the sealing surfaces bear sealingly against surfaces provided for that purpose on the distal and the proximal implant portion when the distal and the proximal implant portions are connected together. The seal and the proximal and the distal implant portions are so designed that, after the definitive connection is made between the distal and the proximal implant portions, a surface pressure prevails between the sealing surfaces of the sealing body and the corresponding surfaces of the two implant portions, which is maintained even when the implant is subjected to mastication forces and, as a consequence of such mastication forces, also suffers elastic deformation in the region of the transition from the proximal to the distal implant portion.

Accordingly, in accordance with the invention, provided between two end faces which, in the case of a finally fitted, two-part stem, in the longitudinal direction of the stem, are in mutually opposite relationship and which are disposed outwardly in relation to the radial direction of the stem, is a seal in the form of a sealing body which is of such dimensions that, upon axial loading on the dental implant, it is not compressed in the axial direction of the stem and, in the event of a lateral loading, always remains compressed by a minimum amount. Thus, when the implant is assembled, the seal is compressed only by the necessary amount so that the implant-abutment connection ensures sealing integrity under all possible circumstances. The degree of compression is dependent on the material and the thickness of the material, when using a greater structural height for the seal, the compressibility of the material could turn out to be less in order to compensate for the movements in the region of the seal.

To fit the sealing body, there is preferably provided a sealing body carrier which serves as a positioning aid for the sealing body and which can already be fitted by the manufacturer of the sealing body so that the dentist who finally fits the implant in the finished condition can easily fit the sealing body by means of the sealing body carrier.

The test described in greater detail hereinafter demonstrates that seals with a sealing body of rigid material cannot ensure the desired sealing integrity:

An implant being investigated was gripped rigidly in a holding device, to the level of the implant shoulder (proximal end of the distal implant portion).

The proximal implant portion was screwed on to the distal implant portion with a defined assembly force, by means of a screw pin.

A force of 100N at a 30° angle to the longitudinal axis of the implant was applied to the proximal end face of the proximal implant portion and elastic (reversible) deformation of the material of the assembled implant components was provoked thereby.

That gave the following measurement results:

The following variations occurred during the action of the force, in the region of the two mutually facing surfaces of the two implant portions:

On the side where the force acted, the dimension of the nominal dimension intended for the seal (defined gap) increases by a value ≥1 μm.

On the side opposite to where the force acted the magnitude of the nominal dimension intended for the seal (defined gap) decreased at the same time by a value ≥50 μm.

The test was carried out with the materials of a titanium alloy (Ti6Al4V) and a ceramic ($ZrO_2$).

Those measurements supported the underlying realization of the invention, that a rigid or plastically deformable seal does not represent any protection against the ingress of bacteria into that region.

Seals which are based on the principle of permanent deformation of a sealing body function only in relation to connections, the components of which are not subjected to the action of any forces.

Tooth implants serve to replace lost mastication members and therefore must carry forces, referred to as mastication forces, and are permanently subjected thereto. When using a rigid or ductile sealing body, gaps which cannot be closed again are already produced when slight extra-axial forces and axial forces which exceed the assembly force of the screw connection occur. Accordingly, those connections cannot be referred to as being bacteria-tight.

The forces required for the surface pressure between the sealing body and the respective implant portion can be produced in two different ways. On the one hand, during the step of connecting the proximal and the distal implant portions, the sealing body can be elastically compressed between the two implant portions if the nature of the connection—for example an axial screw connection—and the nature and arrangement of the seal are suitably selected. Here, an advantageous arrangement is one in which the sealing body is in the form of a circular disc with a central opening therethrough and is arranged between two radially extending surfaces of the distal and the proximal implant portions.

On the other hand, the seal can also have a sealing body which expands after the connection between the distal and the proximal implant portions is made. An arrangement of that kind can best be implemented if the surfaces of the two implant portions are in opposite relationship in the radial direction so that an intermediate space to be filled by the seal between the proximal and the distal implant portions is to be filled by a sealing body which is in the form of a short tube which possibly narrows towards the distal end. It is advantageous if the sealing body has the elastic properties already described or is fitted into the proximal or distal implant portion in its state of being contracted for example by cooling, then the respective other implant portion is connected to the first implant portion and the sealing body is then expanded, for example as a consequence of heating. The same principle can also be applied to a seal in which the sealing body is in the form of a circular disc with a central through opening.

Suitable materials for the sealing body are biocompatible plastic materials, in particular elastomers or duromers. That is also intended to include a particularly suitable blend of rubber and PTFE. That blend preferably contains carbon black as a filler. Thermoplastic elastomers and elastomer alloys (for example polypropylene from the group of polyolefins), thermoplastic materials (for example perfluoro elastomers (PTFE, FKM, FFKM, FFPM) and polyetheretherketone (PEEK) and thermosetting plastic materials (amino or phenoplasts) or a silicone can also be considered as elastic plastic material for the sealing body.

Of those elastomers FFKM which contains PTFE as the base material is particularly suitable as a filler silicic acid. Black coloration of such an elastomer is to be achieved with carbon black and white coloration is to be achieved with titanium dioxide or barium sulphate. Silicic acid alone can already provide for adequate white coloration.

A sealing body which is also particularly suitable is one which is formed in large parts thereof by an elastomer which on its outside is coated with a thermoplastic material or a duromer and more specifically preferably with PTFE. In that case the elastomer permanently maintains the stress and the PTFE is mouth-resistant and provides for permanent sealing integrity.

Another suitable coating material is a dimer such as diapraxylylene which is also known as parylene and which can be applied to surfaces to be coated, in a plasma coating process. Suitable layer thicknesses are between 0.5 μm and 50 μm. Layer thicknesses between 1 μm and 5 μm, for example 3 μm, are particularly suitable. Structural formulae of such a coating material are shown hereinafter:

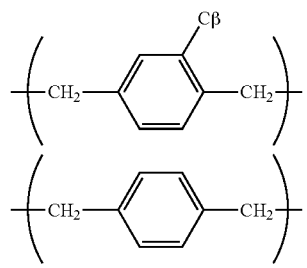

The surface of the parylene coating can additionally be provided with a nano coating of metal such as titanium or silver—also in combination with a ceramic. The coating provides both for bacteria-tightness and at the same time for neutral behavior in relation to cell tissue.

The respective surface to be coated is preferably polarized in order to increase the adhesiveness thereof for the coating. Such a polarization of the surface can be effected in a basically known fashion by means of a plasma process.

In addition it may be advantageous for surfaces of the implant or its constituent parts, in particular the outwardly directed surface of the sealing body, to be polarized in order to achieve better body compatibility. Polarization provides that the adjoining tissue such as for example bone and gums do not or cannot demonstrate rejection behavior in relation to the coating.

In regard to a possibly partially coated sealing body it is desirable if the coated surfaces do not have any sharp edges. Rather, all coated edges should be rounded in order to prevent the coating from flaking off upon deformation of the sealing body.

It is advantageous if the elastic material of the sealing body is elastically stretchable or compressible by at least 5%, better by more than 20%. In an embodiment, by way of example, the spacing, which is predetermined by the abutment surfaces, between the mutually facing surfaces of the two-implant portions is 250 μm so that the seal involves a nominal dimension of 250 μm. In this case the sealing body should be made for example 50 μm over the nominal dimension (250 μm) of the seal so that after assembly a compression of 50 μm (20% compression) already occurs. Those values represent an ideal dimension that it is sought to achieve. The structural height of the seal should be as small as possible in order for aesthetic reasons not to give away structural height for the later tooth crown; in particular dimensions between 0.1 mm and 3 mm are considered as the nominal dimension. In terms of dimensioning, it is crucial that the seal, even under the effect of mastication forces, is deformed only in the range of elastic deformability thereof and also always remains compressed by a minimum amount in partial regions, for example in the event of a lateral loading. Thus, when the implant is assembled, the sealing body is compressed only by the necessary degree so that the implant-abutment connection ensures sealing integrity under all possible circumstances. The degree of compression is dependent on the material and the thickness of the material, when using a greater structural height for the seal the compressibility of the material can turn out to be less in order to compensate for the movements in the sealing region.

For a sealing body which expands when heat is involved, in particular plastic materials with a high coefficient of thermal expansion of more than $75 \times 10^{-6}$/K at 20° are advantageous.

Preferably at least one outside surface of the sealing body, which surface forms the outside surface of the implant, is coated with a metal or ceramic layer in the manner described hereinbefore, in which case the metal-parylene or ceramic layer prevents bacteria from penetrating into seal components which are covered by the metal or ceramic layer. A nano coating, for example with titanium particles, is particularly suitable. The sealing surface itself can directly consist of a biocompatible plastic material or can be coated in the above-mentioned manner. In particular titanium, silver or gold, optionally also in the form of a constituent of an alloy, are considered as the material for the metal layer. All surface materials of the seals are mouth-resistant and sterilizable and do not absorb water or absorb-water only to a very slight degree.

Besides elastic plastic material the sealing body may also include a metal spring or a separate plastic spring element of another plastic material, such as for example PEEK. The spring element can be in the form for example of a plate spring or a ring of a u-shaped, inwardly open cross-section and ensures permanent elasticity and stressing force for the sealing body. A metal spring can be advantageous in particular in relation to a sealing body in which the elastic plastic material at least partially comprises polytetrafluoroethylene (PTFE, Teflon), polypropylene (PP) or also polyetheretherketone (PEEK).

The invention is based on the realization that a two-part dental implant does not have any microgap in the region of the bone emergence point as it is precisely at that location that the implant-abutment connection (IAC) is to be found, that is to say the connection between the proximal and the distal implant portions. That connection causes a microgap, that microgap in turn is the subject of scientific discussion at the present time. It is known that the bone resorbs to about 0.5 mm beneath the implant-abutment connection (if it were exactly at the bone level). It is demonstrated that the tissue adjacent the implant-abutment connection (gum and bone) shows signs of inflammation. It has been shown that there are inter alia polymorphonuclear leucocytes which have priority in relation to bacterially induced processes. The lack of sealing integrity of the IAC and the colonization thereof by bacteria is discussed as the reason for that phenomenon.

The result of bone loss is gingival recession with the consequence of teeth becoming longer (implant crowns). Bone loss represents a major problem in aesthetically demanding regions such as for example in the region of the front teeth.

The sealing body is preferably in the form of a ring which is to be arranged between two abutment surfaces extending perpendicularly to the longitudinal axis of a respective implant portion, and provides for bacteria-tight sealing integrity. Such a sealing body or sealing ring preferably comprises a plastic material which has greater elasticity or lesser hardness than the material of the two implant portions. The two implant portions preferably comprise a body-compatible metal, ceramic or plastic material.

In an advantageous variant of the two-part dental implant the mutually facing surfaces of the two implant portions, between which the sealing body is arranged, extend transversely with respect to the longitudinal axis of the dental implant—that is to say in the radial direction—and parallel to each other. Such surfaces are particularly suitable for arranging between them a sealing body which is in the form of a circular disc with a central opening therethrough. The central opening allows the connection to be made between the proximal and the distal implant portions by means of a screw pin extending in the axial direction of the implant. The screw pin also allows the sealing body to be sufficiently compressed so that the desired surface pressure is produced between its sealing surfaces and the surfaces of the implant portions. The surface pressure is limited in that case by the mutually touching abutment surfaces. In certain situations of use it is advantageous if the sealing body is thicker in the region of its outer edges than in a central region of the seal. In that way the sealing body can be deformed in the region of its edges upon assembly of the proximal and distal implant portions in such a way that its sealing surfaces bear exactly against the surfaces of the two implant portions. In alternative variants the sealing body however can also have sealing surfaces extending in parallel relationship with each other or it can be designed in the manner of an O-ring.

The geometry of the proximal and distal stem portion is preferably such, in the region of the transition between the two stem portions, that the connection between the two stem portions is not only suitable for directly transmitting mastication forces from one stem portion to the other but at the same time is also non-rotational.

In accordance with a preferred embodiment a distal stem portion forming a distal implant portion has a longitudinal opening which is open towards its proximal end and which has an inside wall having a geometry of a circular cross-section and into which are let V-shaped recesses which extend at least approximately in the longitudinal direction of the stem portion and which are open towards the proximal end thereof. A tooth structure stem portion forming a proximal implant portion has at its distal end an outside wall involving a basic geometry of circular cross-section, which fits into the longitudinal opening in the distal stem portion.

Preferably the outside wall of the tooth structure stem portion, in the region of the distal end thereof, has v-shaped projections which are matched to the v-shaped recesses in the distal stem portion in such a way that flank parts of the v-shaped recesses of the distal stem portion co-operate with flank parts of the v-shaped projections of the tooth structure stem portion in such a way that the v-shaped projections of the tooth structure stem portion are pushed like a wedge into the v-shaped recesses of the distal stem portion until in each case two flanks of a v-shaped projection and two flanks of a v-shaped recess come into contact with each other and in that way fix the relative position of the distal stem portion and the tooth structure stem portion without play both in the axial direction and also in the rotational direction when the distal stem portion and the tooth structure stem portion are connected together or have been connected together. The flanks which are in mutual contact act as abutment surfaces and form a defined heightwise abutment. The heightwise abutment is represented by a defined geometrical form of the implant portions themselves. Thus the forces acting from above on the proximal implant portion (proximal stem portion) are transmitted only to the distal implant portion (distal stem portion). If the forces acting were not transmitted by way of the described heightwise abutment but by way of a seal that seal would be destroyed over the duration of the use.

In that respect the configuration of the distal stem portion affords the advantage that it can also receive a tooth structure stem portion without v-shaped projections so that the mutually connected stem portions are as a result admittedly fixed relative to each other with a very high degree of accuracy in the axial direction, but not in the rotational direction. That is advantageous in particular when the stem serves for fixing a bridge structure. Then no further element is necessary for receiving the bridge structure. In the fitting operation the person carrying out the treatment only has to screw a single interconnected element to the implant fixers which are in the mouth of the patient.

The flanks of the v-shaped projections or recesses respectively preferably extend radially outwardly in relation to a cross-sectional plane extending transversely with respect to the longitudinal axis of the implant and thus extend perpendicularly to the peripheral direction. In that way, no radial forces which for example could burst a distal stem portion of ceramic are transmitted by way of the flanks which are in contact after fitting of the implant.

If the distal stem portion comprises a material of greater tensile strength such as for example metal, in particular titanium, the flanks can also be inclined with respect to the above-described, strictly radial orientation, in such a way that flanks belonging to a respective projection of the tooth structure stem portion (that is to say the proximal implant portion) or a respective recess of the distal stem portion (distal implant portion) converge towards each other in an outwardly directed direction. The flanks can be inclined for example through 45° with respect to the radial direction and thus also with respect to the peripheral direction. Accordingly the flanks have a centering action not only in relation to the rotational direction but also in the lateral direction.

The basic geometry of the outside wall of the tooth structure stem portion is advantageously conical at least in the region of the v-shaped projections. Correspondingly the basic geometry of the inside wall of the longitudinal opening of the distal stem portion is advantageously also conical at least in the region of the v-shaped recesses.

For certain situations of use and in particular if the distal stem portion comprises ceramic it may be advantageous if the basic geometry of the outside wall of the tooth structure stem portion and also the basic geometry of the inside wall of the longitudinal opening of the distal stem portion are cylindrical at least in the region of the v-shaped recesses.

In both cases the fit between the outside wall of the tooth structure stem portion and the inside wall of the distal stem portion is preferably a clearance fit at least in the region of the v-shaped recesses.

In addition preferably provided on the distal stem portion and on the tooth structure stem portion are in each case four v-shaped recesses and v-shaped projections respectively, distributed uniformly over the periphery of the respective stem portion. That affords four accurately defined positioning options in the rotational direction between the distal stem portion and the tooth structure stem portion. Alternatively it is also possible to provide more or fewer projections and recesses in mutually corresponding numbers, which are preferably equally distributed over the periphery of the respective stem portion. Suitable numbers are for example 3, 6 or 8.

A projection of a widely opened V-shape (obtuse V-angle) in conjunction with a corresponding recess in the distal stem portion can also be appropriate.

Angles of between 10° and 170° are considered as the V-angles (angle of spread of the respective V-shape). In the sense of a self-centering design configuration, it is advantageous if in that case the V-angle is less than the tip angle of the respective friction cone which is afforded by virtue of the material pairing in the region of the mutually opposite flanks of the v-shaped projections and recesses respectively.

A separate aspect of the invention which can also be implemented in a different manner from that set forth in specific terms hereinbefore provides that, of those end faces of a distal stem portion and a proximal tooth structure stem portion which can encounter each other when the two stem portions are assembled before the two stem portions have assumed their definitive axial position relative to each other, none of the end faces is disposed in a plane extending perpendicularly to the longitudinal axis of the two stem portions. In the case of known two-part stems for tooth implants with means for preventing rotational movement, which generally have such end faces extending perpendicularly to the longitudinal axis, which can butt against each other when stem portions are rotated relative to each other, before the two stem portions are completely pushed into each other in the desired fashion, there is the danger that a proximal tooth structure stem portion is fixed to a distal stem portion in a twisted position, with the consequence that the stem produced by that incorrect assembly operation is of a greater length than is intended because the two stem portions are not yet definitively pushed one into the other. The final fits actually intended for defining the relative axial position of the two stem portions have not yet come into contact with each other in that situation because the twist as between the two stem portions relative to each other means that initially at least one other surface extending perpendicularly to the longitudinal axis of a respective stem portion is in a condition of bearing against an oppositely disposed surface of the respective other stem portion, which is actually not intended to come into engagement with the end face extending perpendicularly to the longitudinal axis of the first stem portion. Automatic correction of the rotational angle error also does not occur because the two surfaces which butt against each other in that way cannot slide against each other in the manner of an inclined plane and in that way automatically correct the rotational angle again.

In the case of known stems for tooth implants, a technician or a physician carrying out the treatment must take care to precisely ensure that the two stem portions are fitted one into each other without any error in terms of rotational angle so that the two stem portions are not fixed relative to each other in a wrong position.

In the case of the stem according to the invention that problem is avoided in that there are no end faces extending perpendicularly to the longitudinal axis of the respective stem portion—apart from the surfaces intended for the purposes of definitive lengthwise end abutment. That is achieved in concrete terms by the v-shaped recesses and v-shaped projections respectively. Other geometrical solutions however can also be envisaged.

That is based on the notion that the surfaces serving as the longitudinal end abutment are arranged on a different radius from the other end faces which serve for positioning purposes in the rotational direction and which in the concrete case considered are formed by the v-shaped projections and recesses.

When the two stem portions are pushed one into the other the inclined surfaces of the oppositely disposed v-shaped recesses and v-shaped projections respectively meet on an inclined plane. When the stem portions are further fitted together the flank surfaces which encounter each other slide one upon the other until the two stem portions have assumed their axial relative end position with respect to each other and have also adopted the correct rotational angle relative to each other.

Suitable materials for the distal and proximal implant portions are in particular metals such as steel or titanium but also ceramic or plastic material.

In order to provide implant portions which are true to shape in a desirable fashion the proximal and distal stem portions are preferably produced either by metal injection molding (MIM) or by hot extrusion molding.

Metal injection molding makes it possible, in just one operating step, namely filling the injection molding mold, to impart to the entire component its definitive geometry which can be of virtually any complexity.

Metal injection molding does not involve the use of a solid metal body but fine material as the starting material for the component to be produced. That powder is mixed with a plastic material-bearing binder and kneaded to form what is referred to as a feedstock. The feedstock is pressed under high pressure at about 100° C. on a commercially available injection molding machine into an injection molding mold (tool) which is a negative representation of the respective stem portion. The green component which is respectively produced in that way, for the proximal or distal stem portion, already involves the desired final geometry but has to be freed of the binder again in the steps that now follow in order to achieve a pure metal component. For that purpose, the binder is removed in a multi-stage chemical and thermal process and at the same time the component is 'baked' by way of a sintering operation at about 1200° C. In that case the metal used is preferably titanium.

If the implant portions should not comprise metal but ceramic, ceramic injection molding (CIM) is considered as a suitable production process. The CIM process functions precisely like the MIM process, the only difference lies in the use of the material. In this context also reference is made to feedstock with ceramic powder instead of metal powder. Accordingly, ceramic constituents of the implant, in particular ceramic stem portions, produced in accordance with an alternative variant by CIM, are preferred.

Alternatively both stem portions can also be produced by cold or warm or hot extrusion molding.

For alternative manufacture of the proximal and the distal stem portions by way of hot extrusion molding, two shaping tools have to be produced for each implant geometry, for production of the connecting region of the implant-abutment connection.

The first shaping tool is produced for the process of hot extrusion molding.

In the hot extrusion molding operation, the titanium is brought into the range of dynamic recrystallization (that means heated to a temperature of between 700° C. and 900° C.).

The operation of shaping the tooth structure component (proximal stem portion) is referred to as warm solid forward extrusion molding or hot solid forward extrusion molding.

The shaping operation for the implant portion (distal stem portion) is referred to as warm cup backward extrusion molding or hot cup backward extrusion molding.

For that purpose a round bar material is cut to length, heated and introduced into the shaping tool. The shaping operation takes place under a high pressing pressure.

A first shaping step produces a result which already comes very close to the final result which can be attained.

The overall geometry of the implant portions which form the implant-abutment connection is already represented after the first shaping step. There are still small tolerances present because of thermal contraction of the cooled workpieces. In addition the surfaces are still dull by virtue of the severe heating of the workpiece, which is necessary for the hot extrusion molding operation. When using titanium the risk of adhesion (the titanium sticking to the tool) does not arise.

In a further shaping step, the precise final form and smooth shiny surfaces in the region of the implant-abutment connection between the two stem portions are then achieved.

The second shaping step involves using a second shaping tool with which cold calibration or warm calibration of the workpieces (proximal or distal stem portion) is carried out.

The second shaping step can be effected at a point which is defined in time during the cooling phase after the first shaping step, at which the workpiece is still at a temperature of between about 400° C. and 450° C.

For the second shaping step the respective workpiece is fully automatically removed from the first shaping tool and introduced into the second shaping tool.

The variation in geometries due to the second shaping step is only very slight as the preferred material titanium is very obdurate in its behavior in the cold and warm states in relation to a shaping procedure. After the metal lattice of titanium has begun to flow briefly and locally, it becomes brittle quite quickly upon further shaping. The titanium structure is destroyed in the event of excessively substantial cold or warm shaping. With a very slight degree of shaping however, besides a defined final form for the workpieces in the region of the implant-abutment connection, an increase in hardness is also achieved by local cold consolidation of the workpieces.

The shaping procedures are respectively terminated after the second shaping step and the geometry described hereinbefore in relation to the implant-abutment connection between two stem portions is finished.

The tool set required for the hot extrusion molding operation with the two above-described shaping steps, for shaping a respective implant component, comprises in each case two shaping tools.

For production of the shaping tools, firstly graphite bodies are produced on a 5-axis micromilling apparatus. To produce the shaping tool, the graphite bodies are eroded into a block of hardened steel by means of spark erosion.

The resulting surfaces of the shaping tool, which subsequently shape the mass-produced parts, have to be polished by hand in a very laborious process.

Possibly it may be necessary for one or both workpieces (proximal or distal stem portion) to be further worked in regions outside the implant-abutment connection.

The optionally required operation of shaping the workpieces to give the desired final shape is achieved by cutting machining. That shaping operation concerns the geometries of proximal regions of the proximal stem portion for corresponding tooth structures, for example crowns, as well as the geometries of distal regions of the distal stem portion for providing an artificial tooth root.

For a cutting machining shaping operation of that nature, the workpieces must be gripped in a workpiece holder of a suitable machine. For that purpose it is appropriate for the workpieces to be gripped at the exact geometries of the workpieces, that are produced by the hot extrusion molding operation, and held thereby during the cutting machining process.

In order to exclude inaccuracies each workpiece is clamped only once for the cutting machining operation.

A suitable machine for the cutting machining shaping procedure is a turning machining center, that is to say a machine on which all necessary cutting machining steps can be carried out in succession.

To achieve the final shape for the tooth structure and the implant, in general it is necessary to use both stationary tools (in the turning operation) and also rotating tools (in the milling operation). An axial through bore in the proximal stem portion and an axial bore with a female screwthread for receiving a screw pin connecting the two stem portions is also formed by boring in that process.

BRIEF DESCRIPTION OF THE DRAWINGS

The Figures show in greater detail an embodiment by way of example of a stem according to the invention for a dental implant including some variants of the sealing body as well as an embodiment by way of example of a sealing body carrier as an auxiliary tool for assembly of the two stem portions. In the drawings:

FIGS. 16a to b shows the principle of the mutually facing abutment surfaces which limit maximum compression of the seal.

DETAILED DESCRIPTION OF THE INVENTION

In the two-part dental implant shown in the specific embodiments a proximal implant portion is formed by a tooth structure stem portion 10 and a distal implant portion is formed by a distal stem portion 20.

Figure 1:
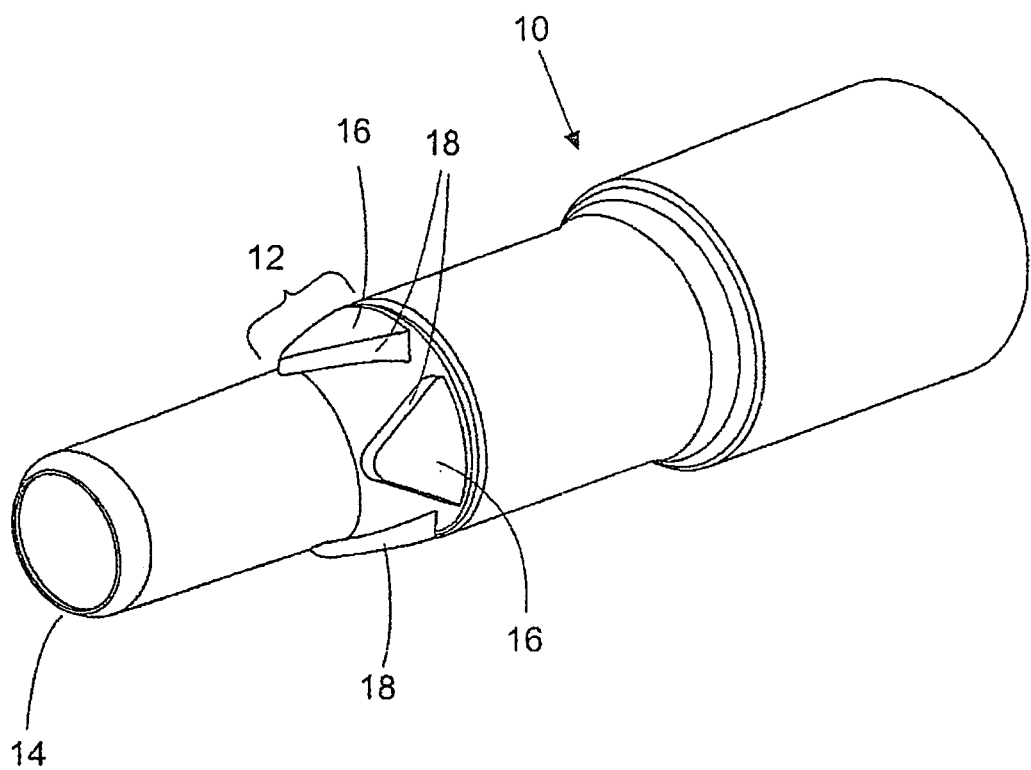
FIG. 1 shows a perspective view of a tooth structure stem portion as a proximal implant portion.

As the perspective view of the tooth structure stem portion 10 shown in FIG. 1 illustrates, it has a longitudinal part 12 of a conical basic geometry which narrows towards the distal end 14 of the tooth structure stem portion 10. The cone angle is 10°. In the region of that conical longitudinal part 12 the tooth structure stem portion 10 has a total of four v-shaped projections 16 which face with their tips towards the distal end 14 of the tooth structure stem portion 10. The four v-shaped projections 16 act as triangular prongs and are symmetrical and are arranged at equal spacings from each other around the periphery of the conical longitudinal part 12 of the tooth structure stem portion 10. That affords eight flank surfaces 18 which face inclinedly towards the distal end 14 of the tooth structure stem portion 10.

Figure 2:
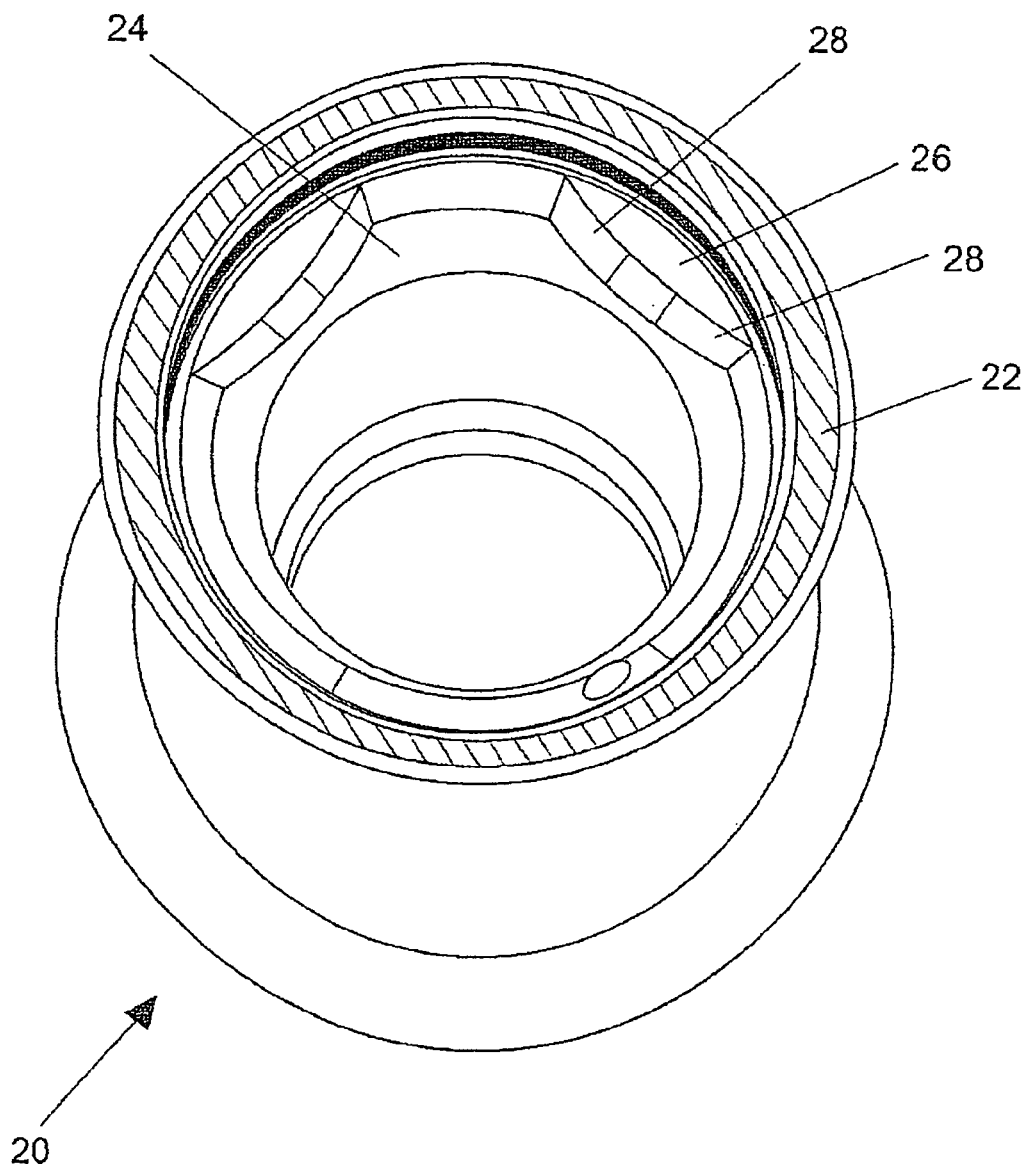
FIG. 2 shows a perspective view of the distal stem portion as a distal implant portion.

FIG. 2 is a perspective view showing the distal stem portion 20. It has a longitudinal opening which is open towards its proximal end 22 and which has an inside wall 24 which is also of a conical basic geometry. Cut into the inside wall 24 are four v-shaped recesses 26 which have flank surfaces 28 facing inclinedly towards the proximal end 22 of the distal stem portion 20.

Figure 3:
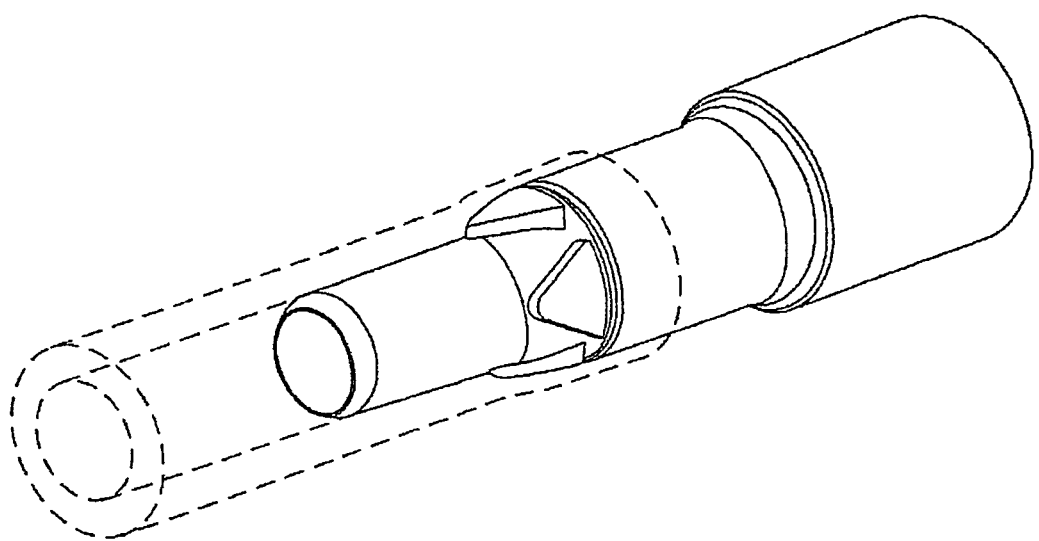
FIG. 3 shows a perspective view of the stem with interconnected distal stem portion and tooth structure stem portion, wherein the distal stem portion is shown in partially dotted line form.
Figure 4:
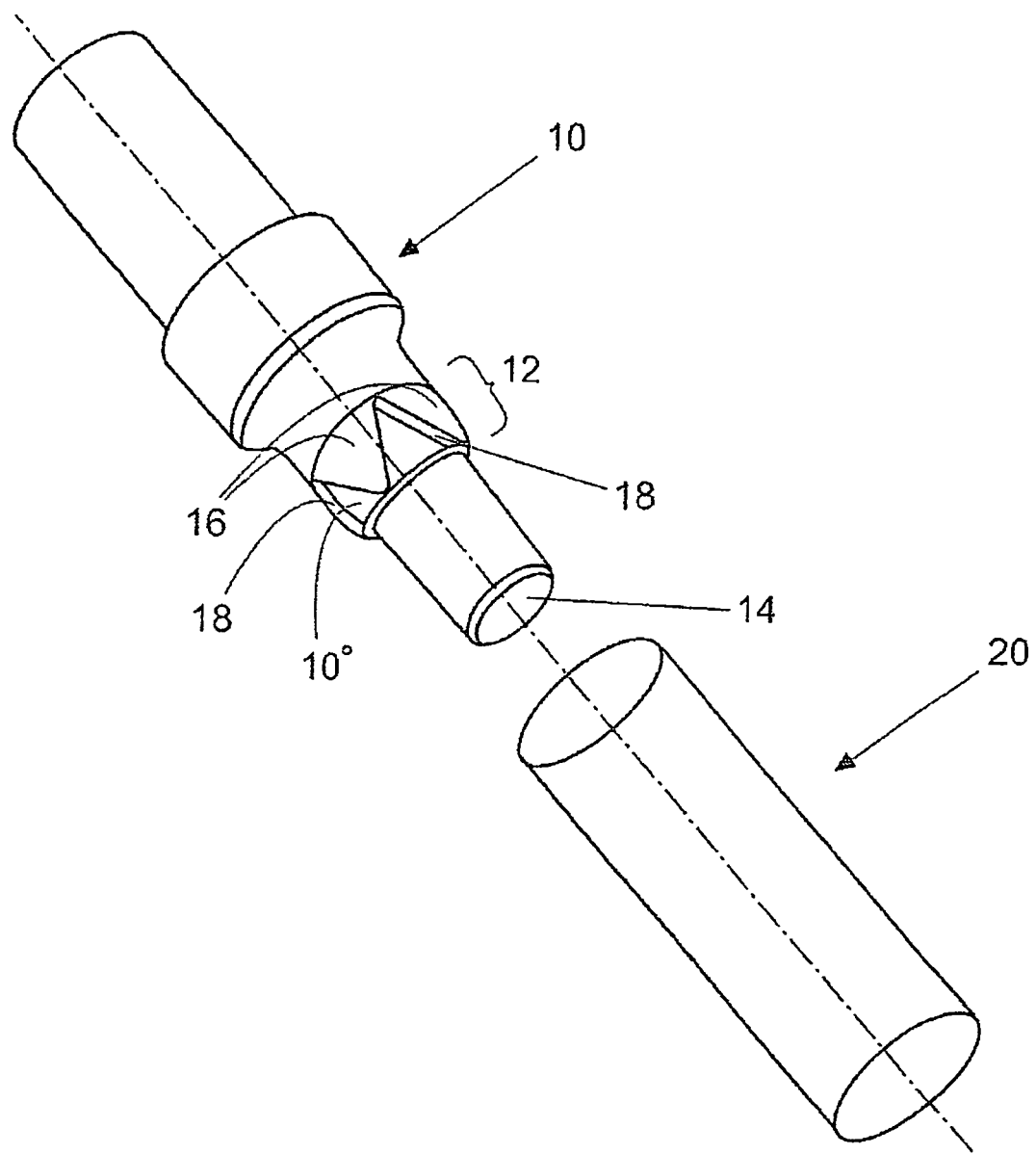
FIG. 4 shows a perspective exploded view of the distal stem portion and the tooth structure stem portion.
Figure 5:
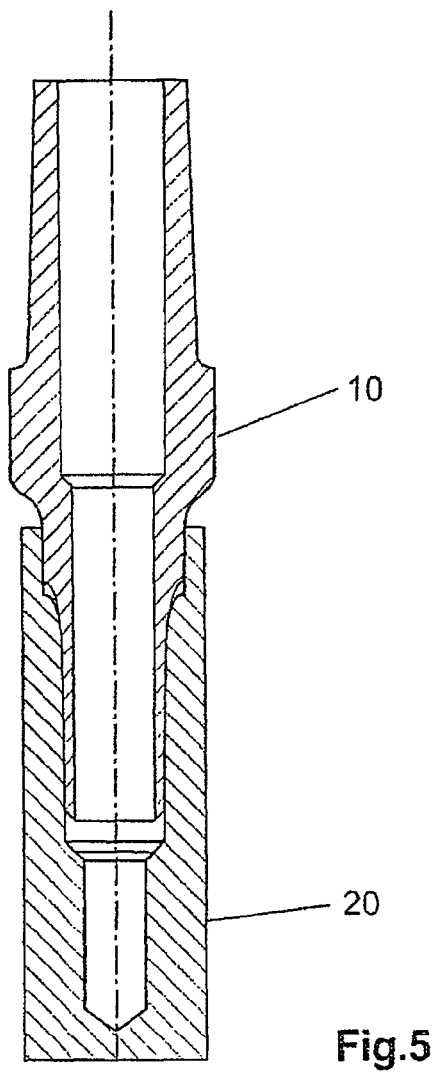
FIG. 5 shows a longitudinal section through the stem.
Figure 6:
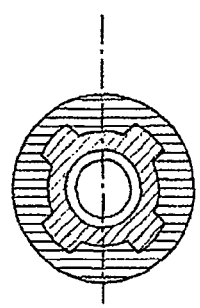
FIG. 6 shows a cross-section through the stem of FIG. 5.
Figure 7:
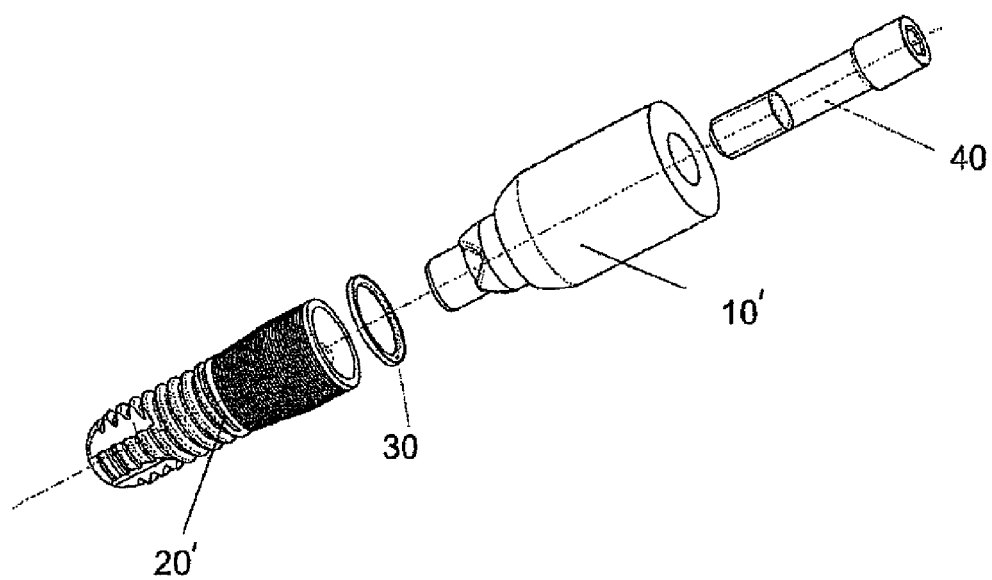
FIG. 7 shows an exploded view of the stem with all its constituent part, namely the proximal and distal stem portion, the sealing body and a screw pin for connecting the stem portions to form the stem.
Figure 8:
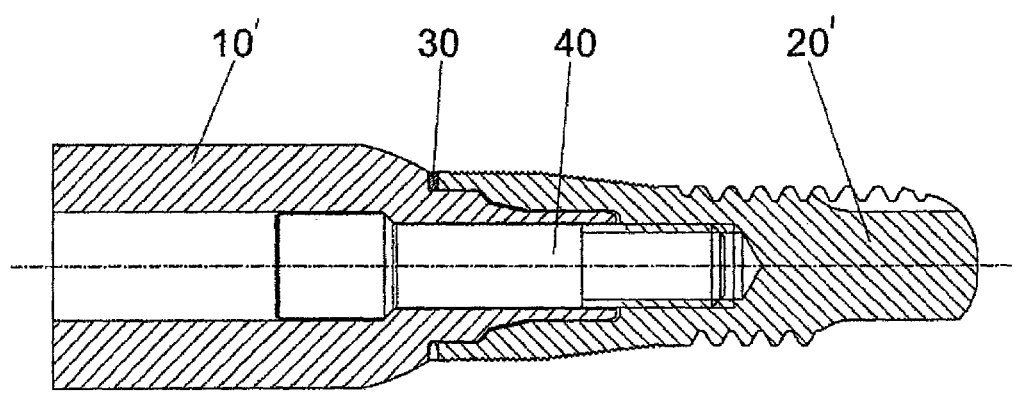
FIG. 8 shows a longitudinal section through the fully assembled stem of FIG. 7.
Figure 12:
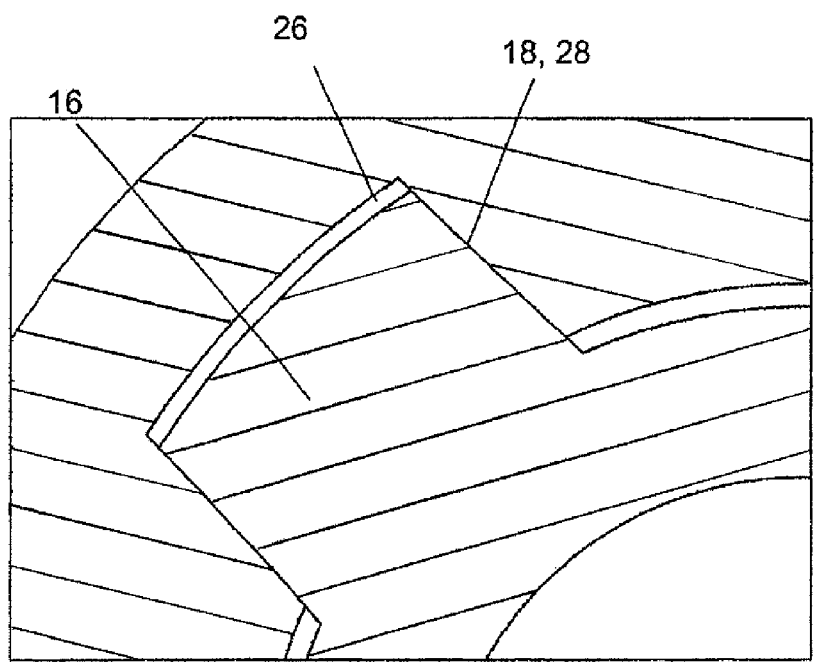
FIG. 12 shows a lateral cross section through the proximal and distal stem portions.

When the distal stem portion 20 and the proximal tooth structure stem portion 10 are connected together (see FIG. 3), the relative position of the two stem portions is very accurately defined both in the axial direction and also in the rotational direction, by flank surfaces 18 and 28 respectively which bear snugly against each other. The inclined flank surfaces 18 and 28 respectively of the v-shaped projections and recesses respectively thus form mutually facing abutment surfaces which limit the approach of the two mutually facing surfaces 32 and 34 (see FIG. 13) and thus the maximum compression of the seal 30 (FIGS. 7 and 8). That is pictorially illustrated in FIG. 12. In particular FIG. 12 shows how the surfaces 18 and 28 are in contact and thus form a longitudinal abutment, in the final assembled condition of the dental implant.

Exact centering of the two stem portions is effected in the assembly operation by the respective mutually opposite inclined flank surfaces 18 and 28 respectively of the v-shaped projections and recesses respectively. Upon inserting the tooth structure stem portion 10 into the longitudinal opening of the distal stem portion 20 the inclined flank surfaces 18 and 28 of the projections and recesses respectively meet on an inclined plane. Thus upon further insertion into the longitudinal opening of the distal stem portion 20 the tooth structure stem portion 10 slides until it reaches its axial final position and in that situation rotates until all mutually opposite flank surfaces 18 and 28 are in uniform contact with each other. As a result the tooth structure stem portion 10 is forced into its desired final position without impediment to its sliding movement and can then be fixed by a screw pin 40 extending in the longitudinal direction of the stem (see FIG. 7). That screw pin 40 is tightened with a force of 30 Ncm.

The corresponding flank surfaces 18 and 28 which serve simultaneously as a longitudinal abutment and as a rotation-preventing securing means are then advantageously sunk in the interior of the longitudinal opening of the distal stem portion 20 and are not disposed in the region of the implant shoulder, as in other systems. The implant shoulder can thus be held at exactly the same level.

In the variants shown in FIGS. 1 to 6 no particular measures are shown for making the transition from the proximal tooth structure stem portion to the distal stem portion bacteria-tight in the region of the outside contour of the finished assembled stem.

In accordance with the variant shown in FIG. 7, provided for that purpose is a sealing ring 30 arranged between an outwardly disposed end face 32 of the proximal tooth structure stem portion 10' and an outwardly disposed end face 34, which is in opposite relationship thereto, of the distal stem portion 20'. When the stem is in the final assembled condition, that is to say when the proximal tooth structure stem portion 10' and the distal stem portion 20' have assumed their definitive axial relative position with respect to each other, the sealing ring 30 is compressed in the axial direction. The sealing ring 30 comprises a biocompatible plastic material.

FIG. 7 shows the essential component parts of the stem according to the invention for a dental implant, as an exploded view, more specifically, the proximal stem portion 10', the distal stem portion 20', the sealing body 30 for sealing off the transition between the proximal and distal stem portions and the screw pin 40 serving to screw the proximal and distal portions together.

The longitudinal section through the stem according to the invention for the dental implant in FIG. 8 has all of the essential component parts in the final assembled condition, with a correspondingly compressed sealing body 30.

Figure 9:
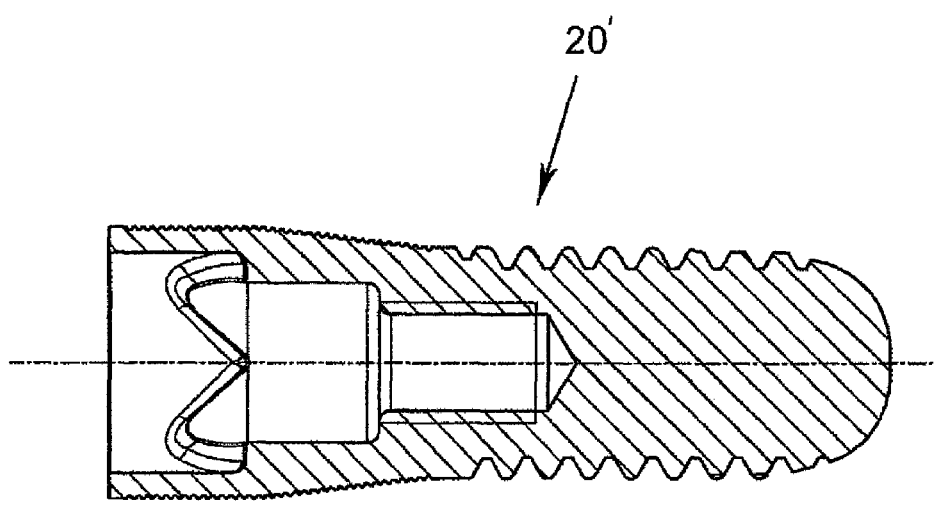
FIG. 9 shows a longitudinal section through the distal stem portion.
Figure 10:
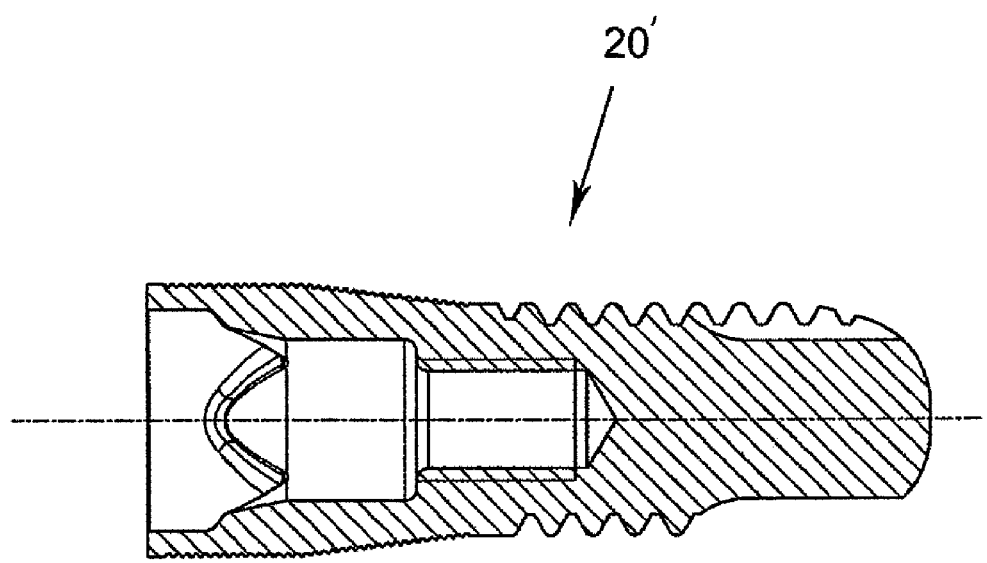
FIG. 10 shows a further longitudinal section, turned through 30° with respect to FIG. 8, through the distal stem portion.
Figure 11:
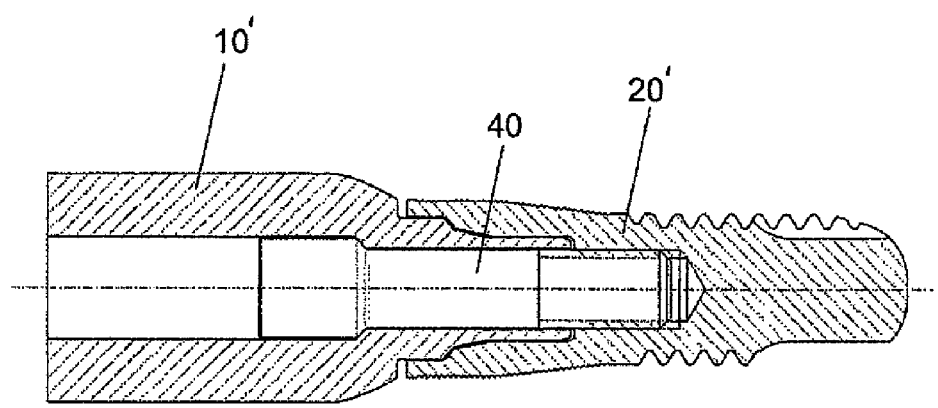
FIG. 11 shows a section similar to FIG. 8 but without the sealing body.

FIGS. 9 to 11 show respective longitudinal sections of individual component parts.

FIG. 12 shows how the flanks 18 and 28 of the projections 16 on the proximal stem portion 10 and the recesses 26 on the distal stem portion 20 respectively co-operate in such a way that centering is effected by way of those flanks and not for example by way of the peripheral surfaces, which are to be found therebetween, of the stem portions 10 and 20.

Figure 13:
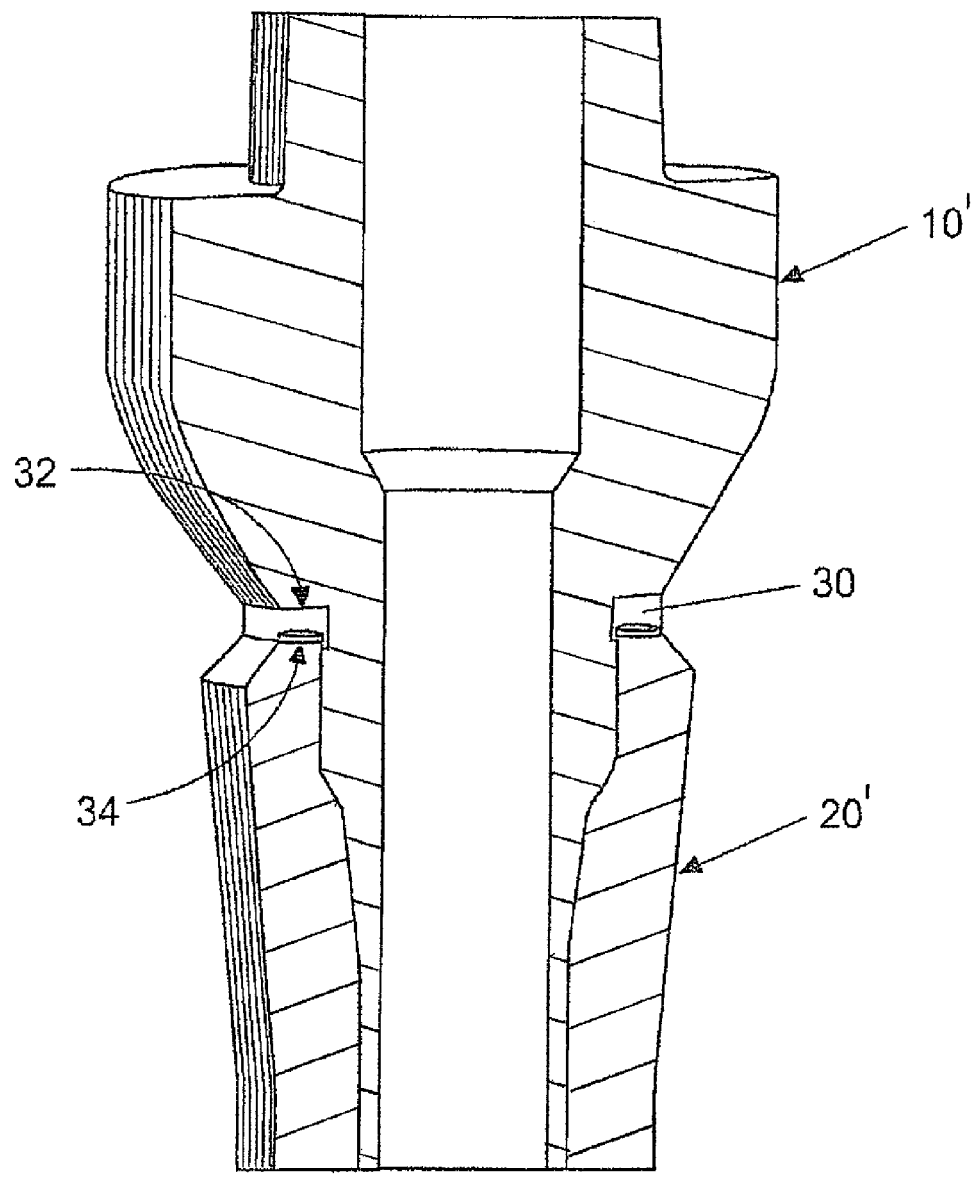
FIG. 13 shows a sectional view of a preferred configuration of the surfaces, which are disposed outwardly with respect to the longitudinal axis of the stem, of the distal stem portion and the proximal tooth structure stem portion and a sealing ring.

The view of the transition between the tooth structure stem portion 10' and the distal stem portion 20', which is a partly sectional perspective view on an enlarged scale in FIG. 13, shows that the outside contour of the fully assembled stem, in the transitional region from the tooth structure stem portion 10' to the distal stem portion 20', does not have any gaps, in respect of which there is a risk of bacteria permanently collecting therein.

Figure 14:
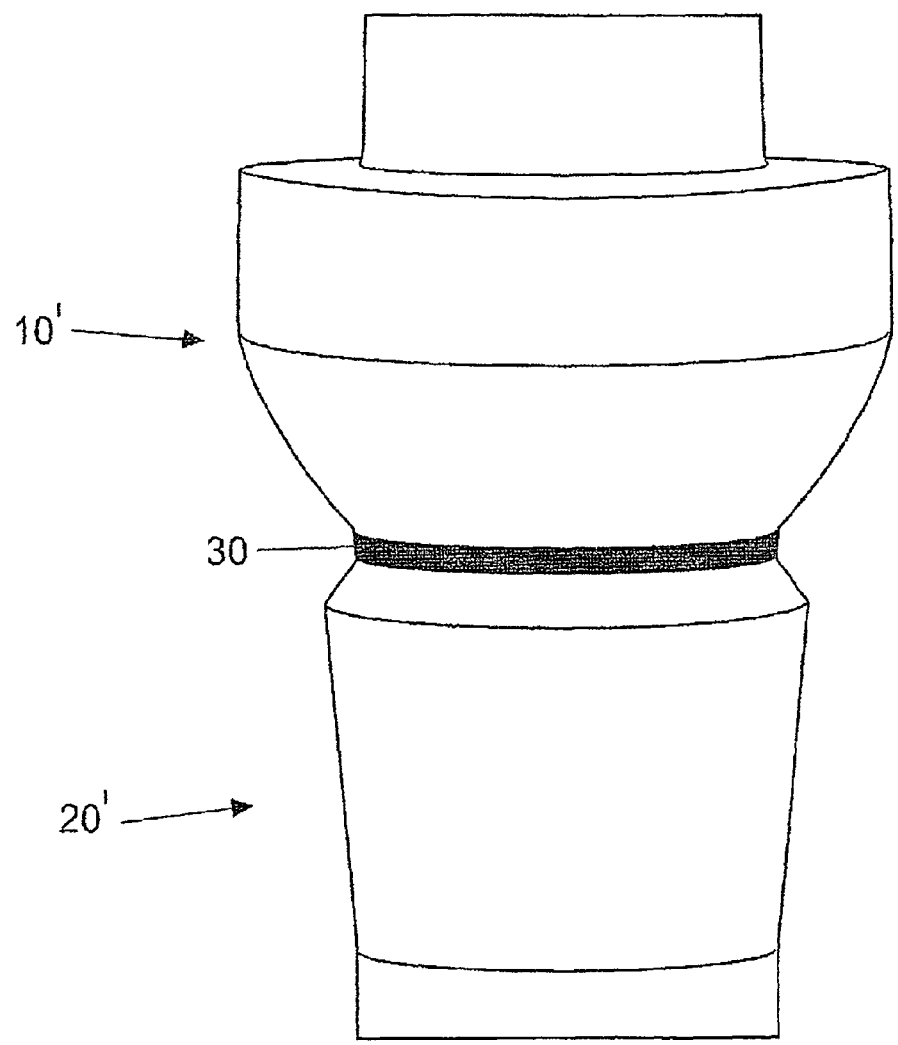
FIG. 14 shows a perspective outside view of the outside contour of a preferred transition from the proximal to the distal stem portion.

That can be seen equally from the outside view of the transition between the tooth structure stem portion 10' and the distal stem portion 20' in FIG. 14.

Figure 15:
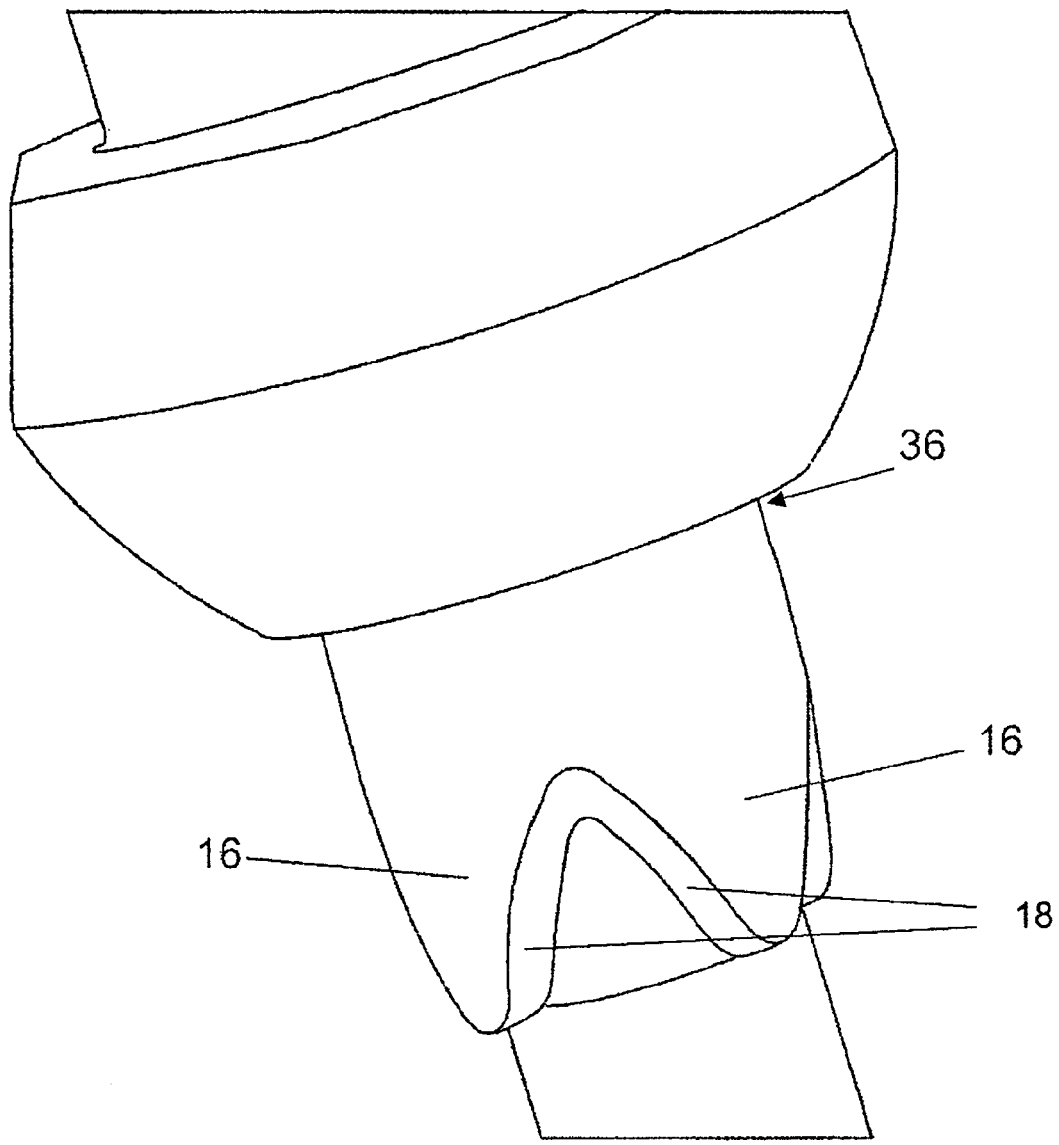
FIG. 15 shows a perspective detail view on an enlarged scale of a variant of a tooth structure stem portion in accordance with the embodiments of FIGS. 7 and 8.

FIG. 15 shows a perspective detail view on an enlarged scale of the proximal tooth structure stem portion 10'. The Figure shows a seat 36 for the sealing body 30 as well as the v-shaped projections 16 which have already been discussed with reference to FIGS. 1 to 6.

Figure 17:
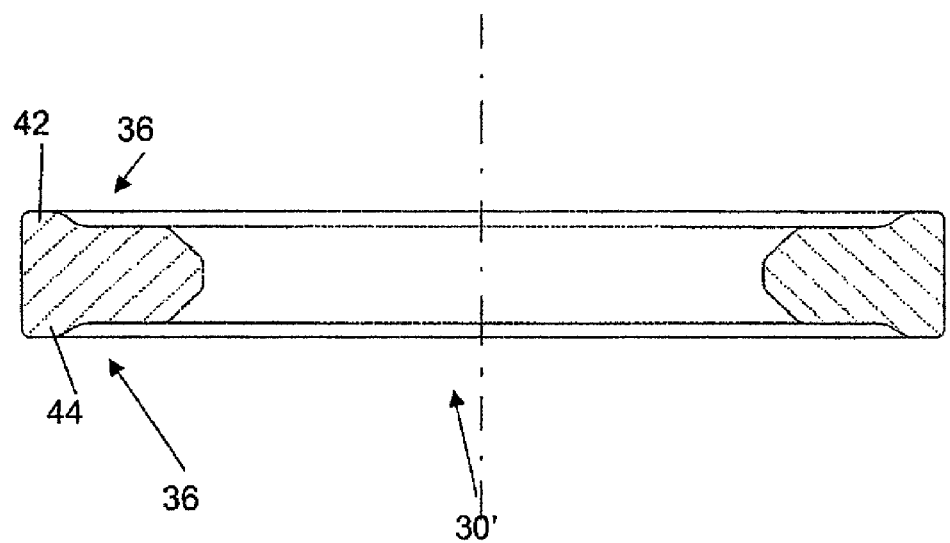
FIG. 17 shows a preferred annular sealing body of an elastomer.
Figure 18:
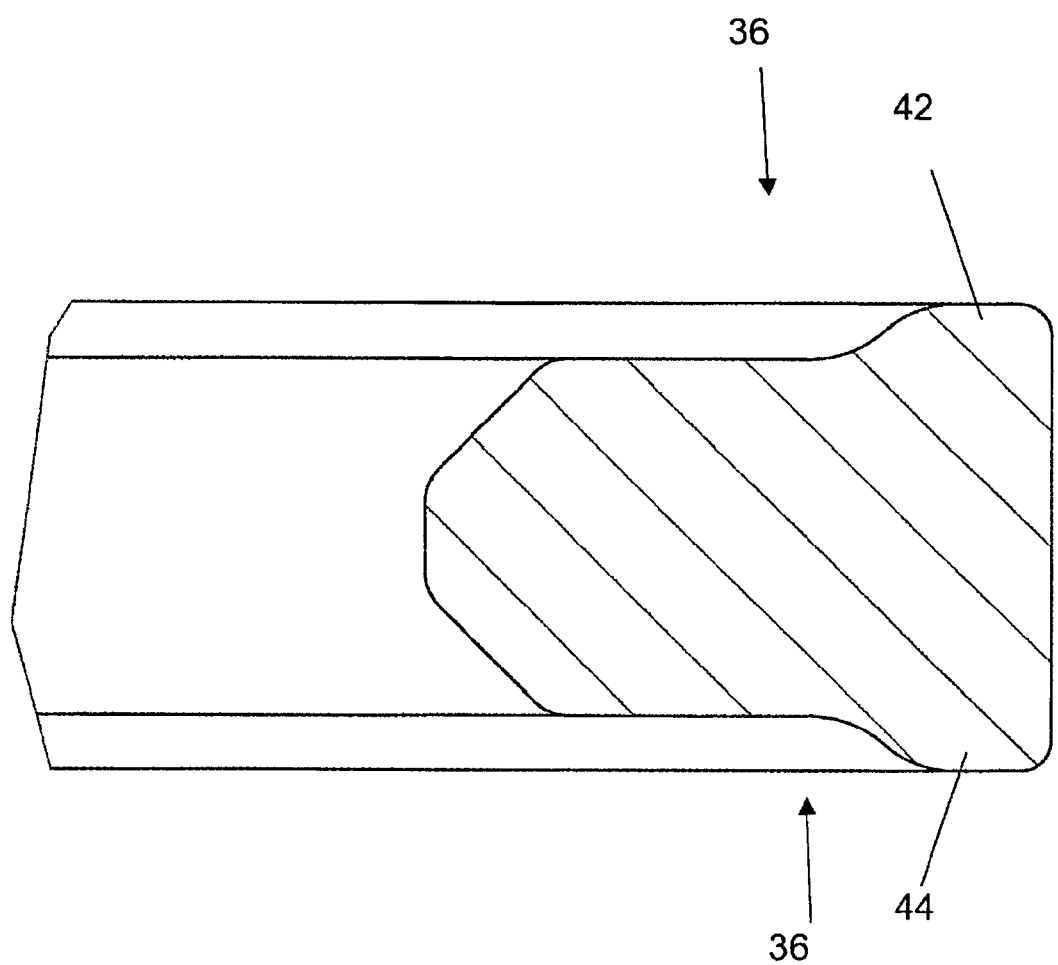
FIG. 18 shows a detail view on an enlarged scale from FIG. 17.

FIGS. 16a and 16b shows how the flanks 18 and 28 act as abutment surfaces in the longitudinal direction and thus provide for defined compression of the sealing body 30 (see also FIG. 12);

FIGS. 17 and 18 show a preferred sealing body 30' comprising an elastomer such as FFKM, in cross-section. It will be seen that the sealing surfaces 36 of the sealing body 30' are not flat but project in the axial direction of the implant at the outer edge of the sealing body and in that way form ridges 42 and 44. Those ridges are deformed when the proximal and distal implant portions are tightly connected and thus produce a secure sealing effect.

Figure 19:
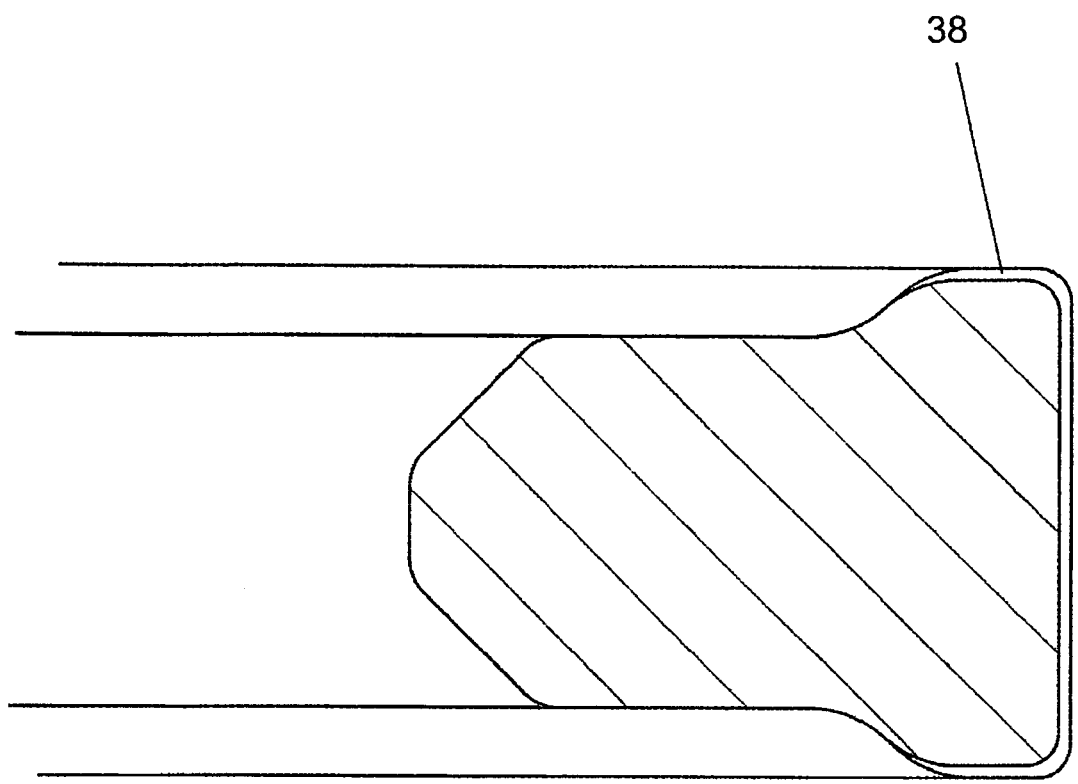
FIG. 19 shows a sealing body as shown in FIGS. 17 and 18, partially coated with a nano coating.

FIG. 19 shows the sealing body 30' of FIGS. 17 and 18 with a coating 38 of parylene, as is described hereinbefore. It can also be seen from FIG. 18 that the coated edges of the sealing body 30' are rounded in order to prevent the coating from flaking off in the region of those edges.

Figure 20:
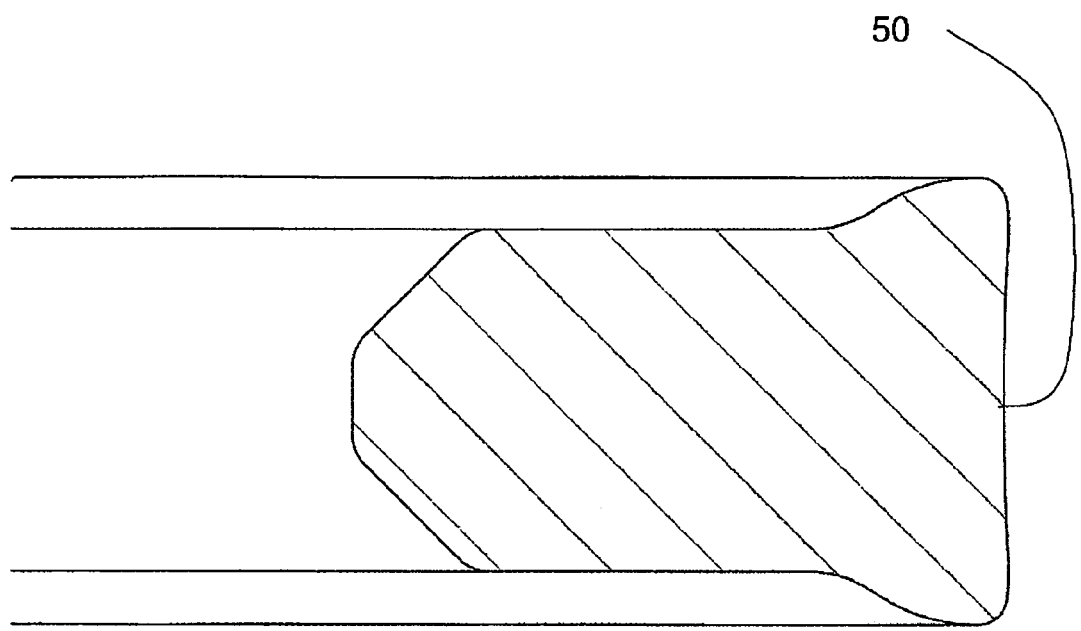
FIG. 20 shows a sealing body similar to that of FIGS. 17 and 18 with a concave outer peripheral surface.

FIG. 20 shows that the outer peripheral surface 50 of the sealing body can be of a concave shape so that it is straightened to be as approximately straight as possible as a consequence of compression of the sealing body after assembly of the stem according to the invention.

Figure 21:
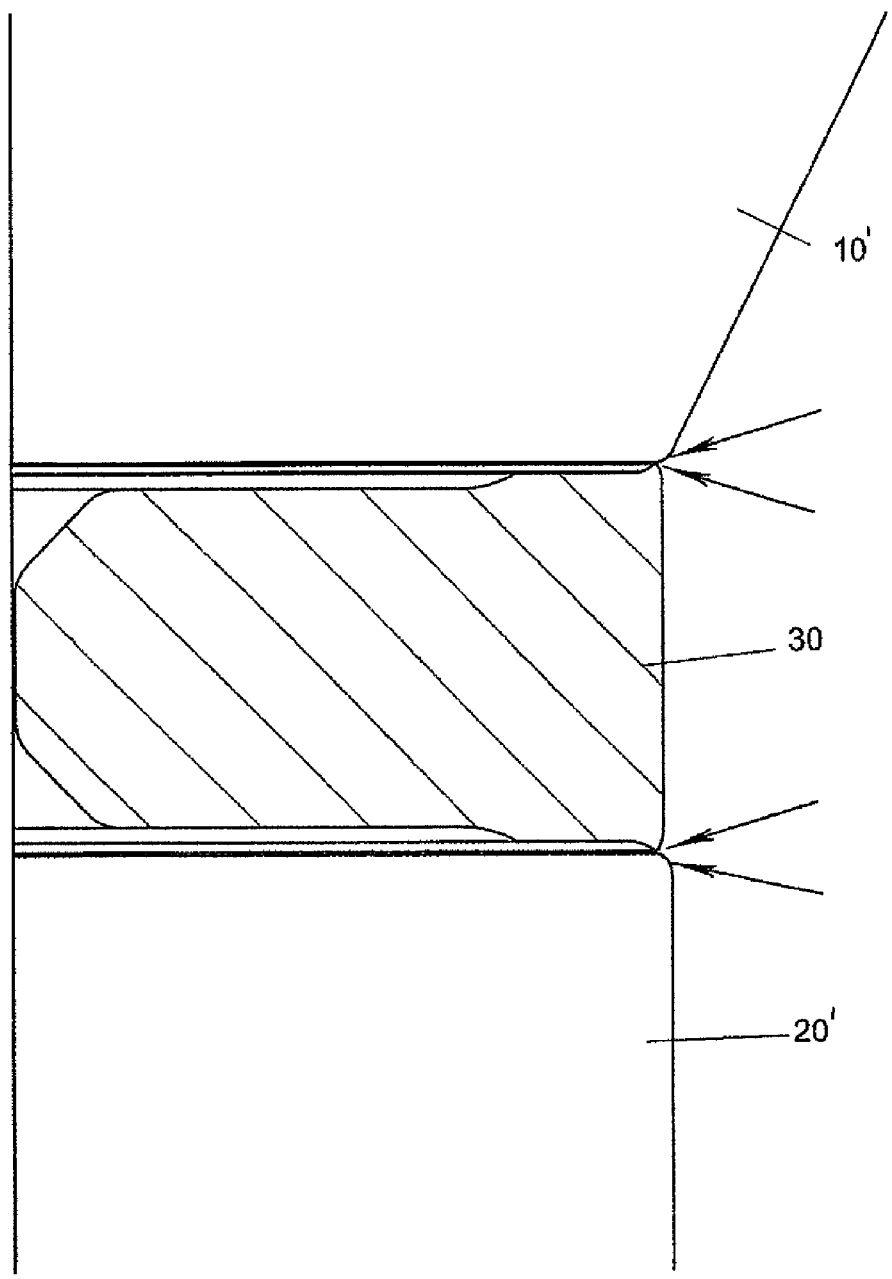
FIG. 21 shows the sealing body 30 in its fully assembled, compressed condition between the proximal and distal stem portions.

FIG. 21 shows the rounding of the edges of the sealing body 30 and the stem portions 10' and 20' at the locations marked by arrows.

Figure 22:
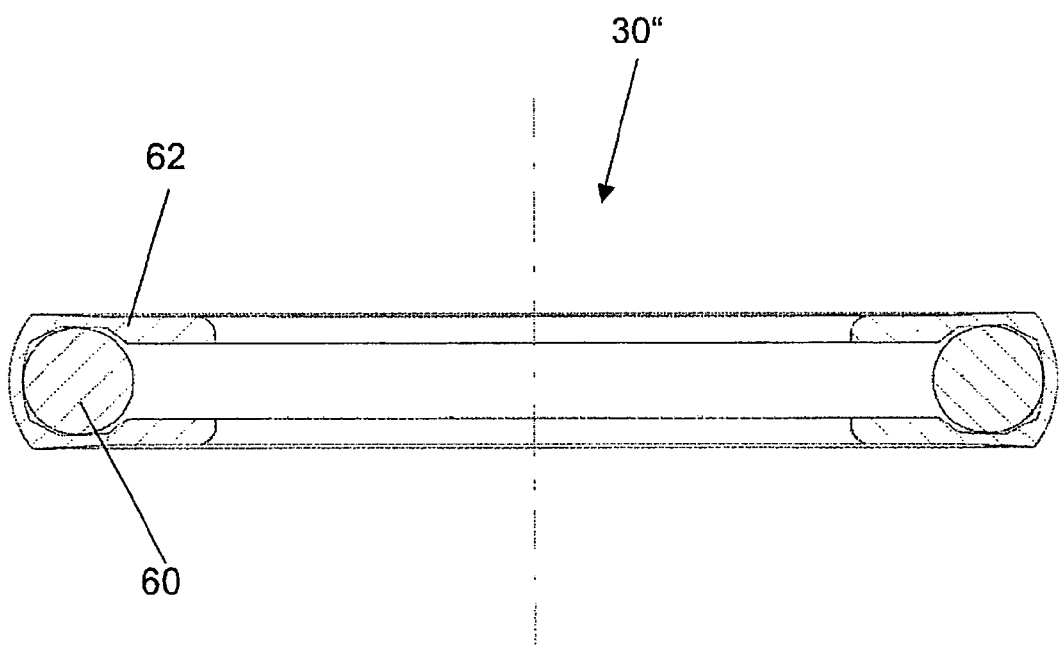
FIG. 22 shows a cross-sectional view of an alternative sealing body.
Figure 23:
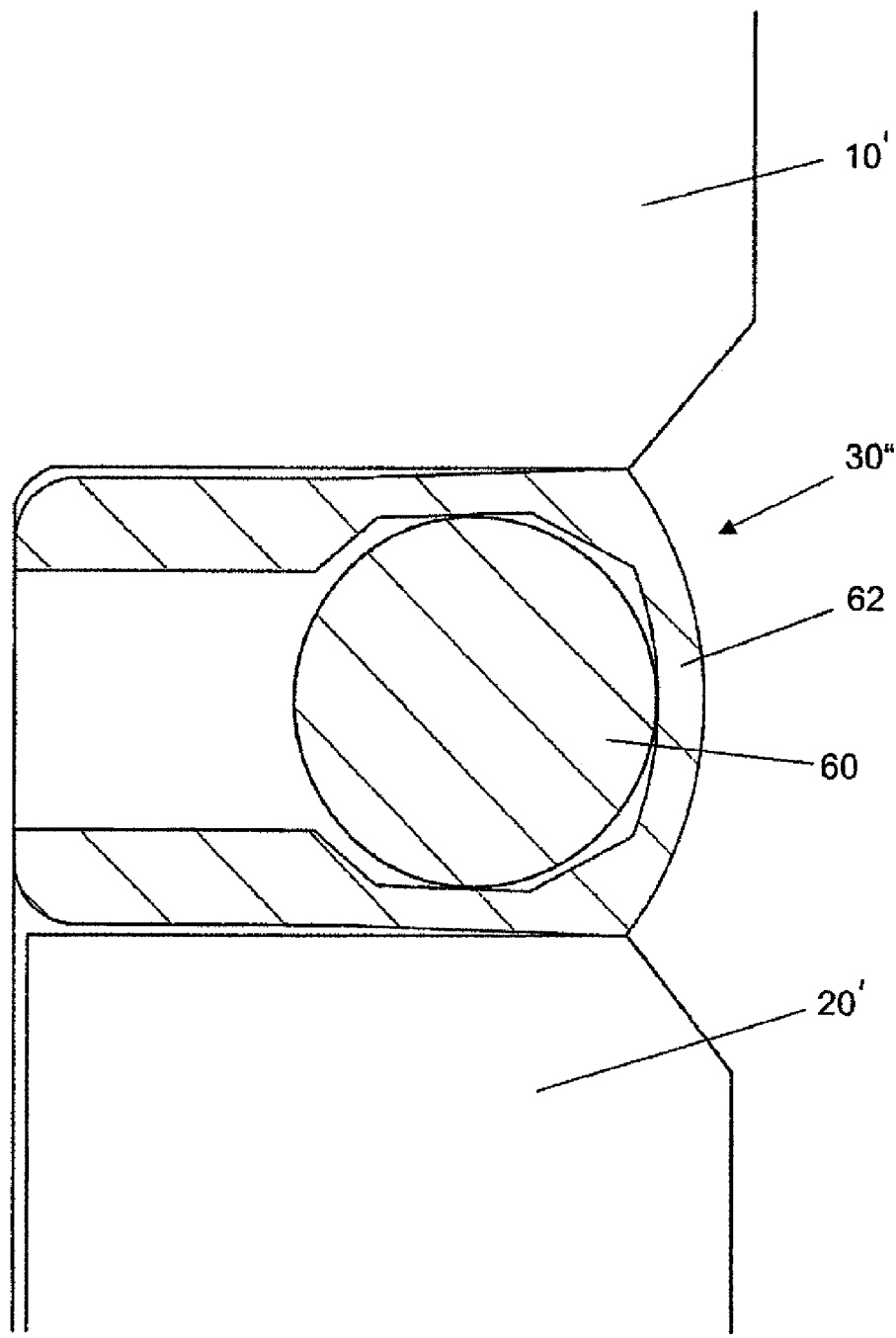
FIG. 23 shows the alternative sealing body of FIG. 22 in its fully assembled, compressed condition between the proximal and distal stem portions.
Figure 24:
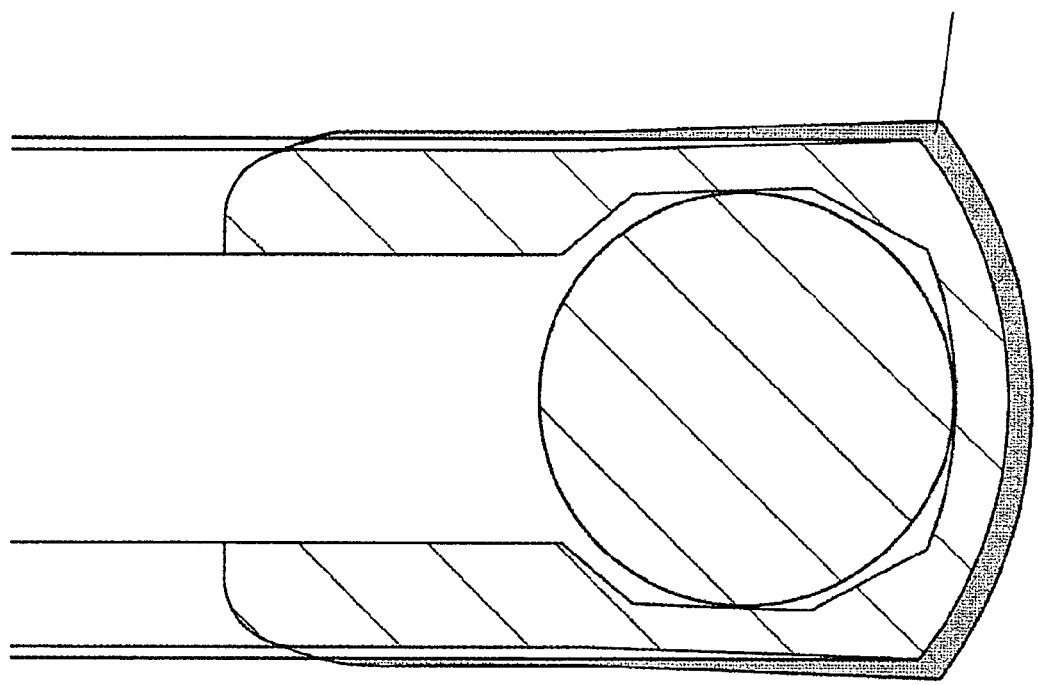
FIG. 24 shows the alternative sealing body of FIG. 22 with a nano coating.

FIGS. 22 to 24 show an alternative sealing body 30" with an elastomer body 60 in the form of an O-ring which is fitted into a ring element 62 of inwardly open, u-shaped cross-section.

FIG. 22 shows a view in cross-section of the alternative sealing body 30". FIG. 23 is a view on an enlarged scale showing a part of the alternative sealing body 30" in the fitted condition between the proximal stem portion 10' and the distal stem portion 20'. FIG. 24 shows that the alternative sealing body 30" can also have a coating 38 for example of parylene.

Figure 25:
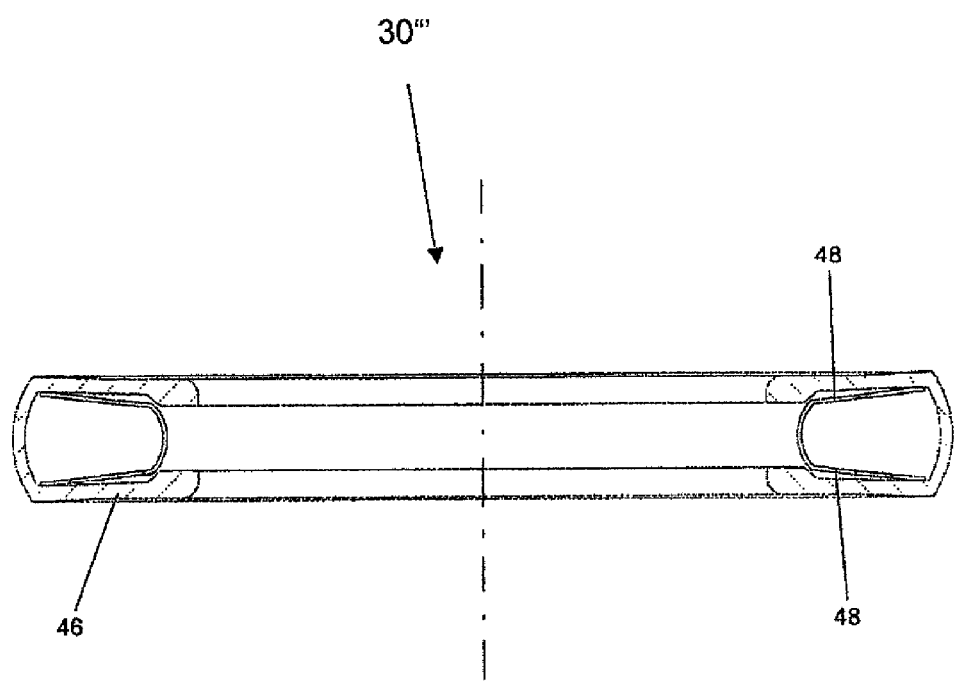
FIG. 25 shows a view in cross-section of a second alternative sealing body with nano coating and integrated metal spring.
Figure 26:
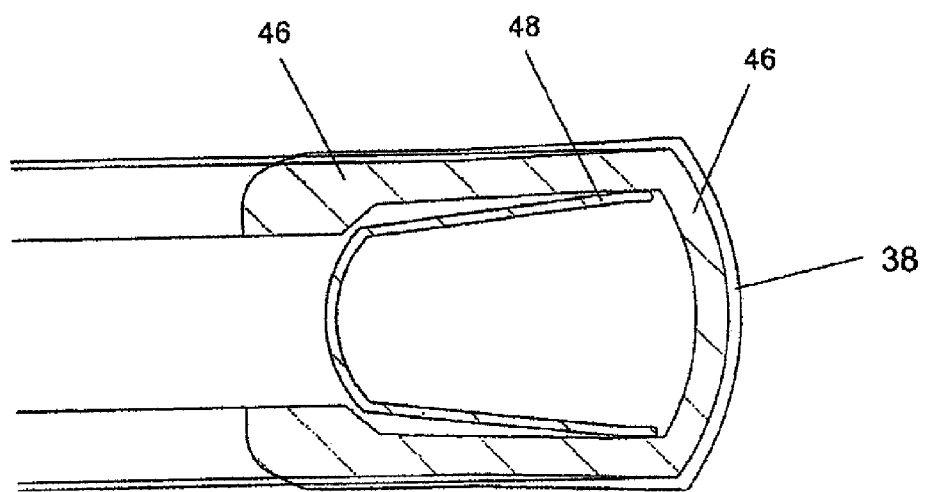
FIG. 26 shows an enlarged portion of the second alternative sealing body of FIG. 25.
Figure 27:
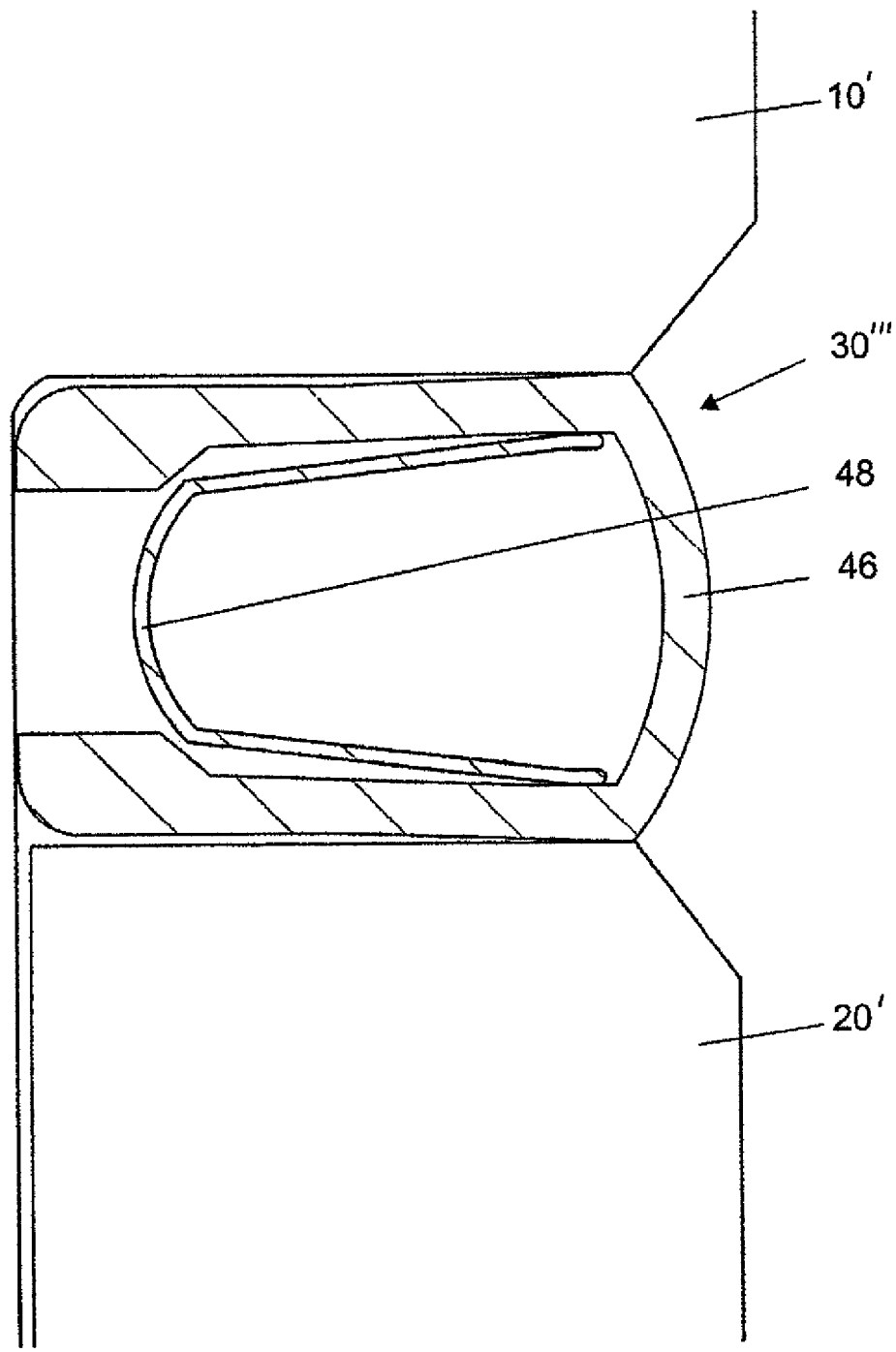
FIG. 27 shows the alternative sealing body of FIGS. 25 and 26 in its fully assembled, compressed condition between the proximal and the distal stem portions.

FIGS. 25 to 27 show by way of example a further alternative variant of a sealing body 30''' which has a metal spring 48 in its interior. The metal spring 48 is disposed in an elastic plastic material body 46 which is of an annular configuration and which is of a u-shaped, inwardly open cross-section. The plastic material body preferably comprises PTFE and the metal spring 48 comprises stainless steel. As FIG. 26 shows the plastic material body 46 can have a coating 38, for example of parylene, on its outside. On its outside, the plastic material body 46 is covered with a layer 38 which is a few nanometers thick and which in the illustrated preferred variant contains titanium particles. The thickness of the layer 38 is shown in greatly exaggerated form in the Figure in order to make the layer visible. A nano coating of that kind can be provided on all outside surfaces of the sealing body, more specifically, irrespective of the external form of the sealing body.

In alternative variants the springs can also comprise another resilient material, for example titanium or a plastic material such as PEEK. The springs can also be of a different form as long as they exert a spring action in the longitudinal direction of the sealing body, as indicated by the dash-dotted line (see FIG. 25).

Figure 28:
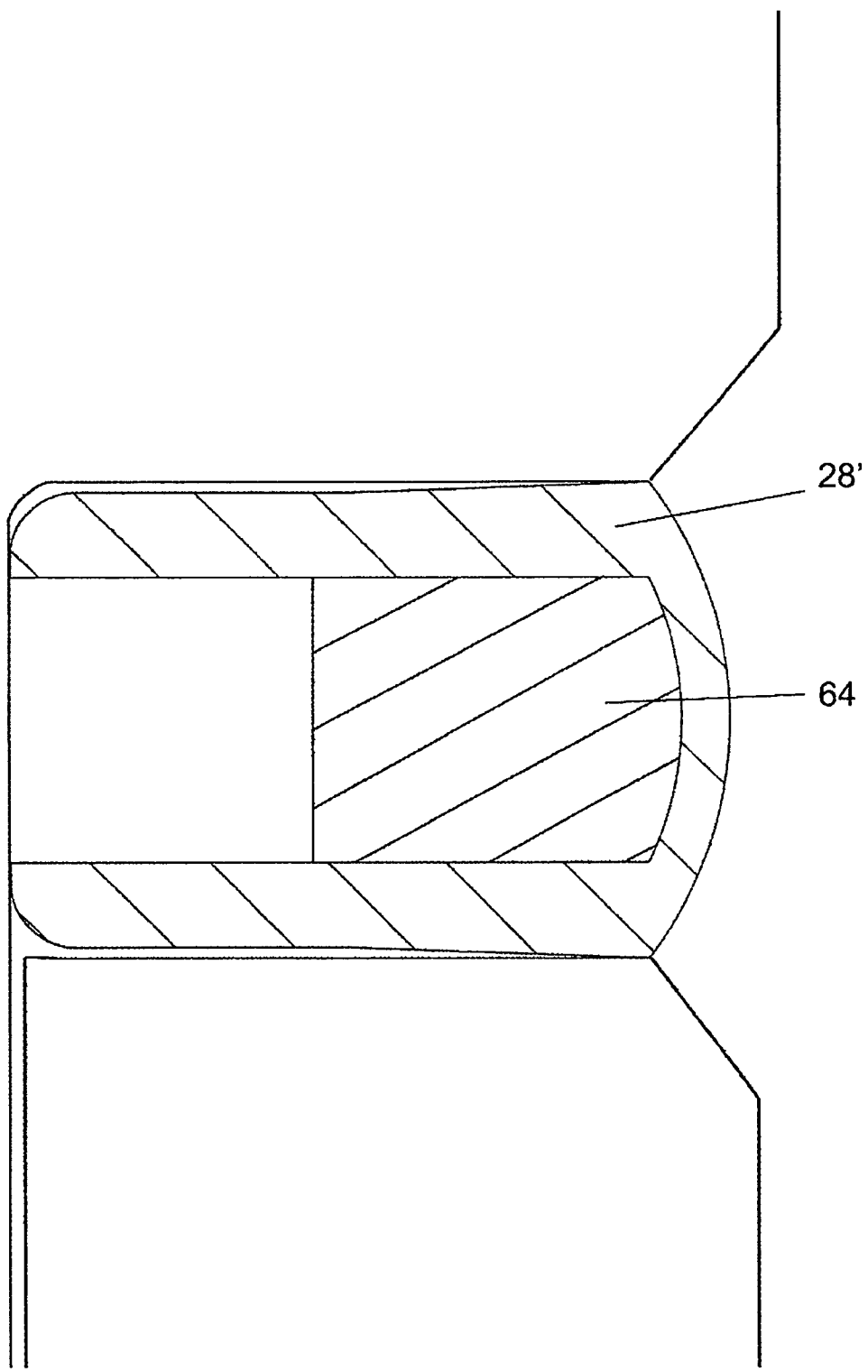
FIG. 28 shows the second alternative sealing body of FIGS. 25 and 26 with a nano coating.

FIG. 28 shows a sealing body in which an annular plastic material body 28', for example of PTFE, of inwardly open, u-shaped cross-section, is partially filled with elastomer 64.

Figure 29:
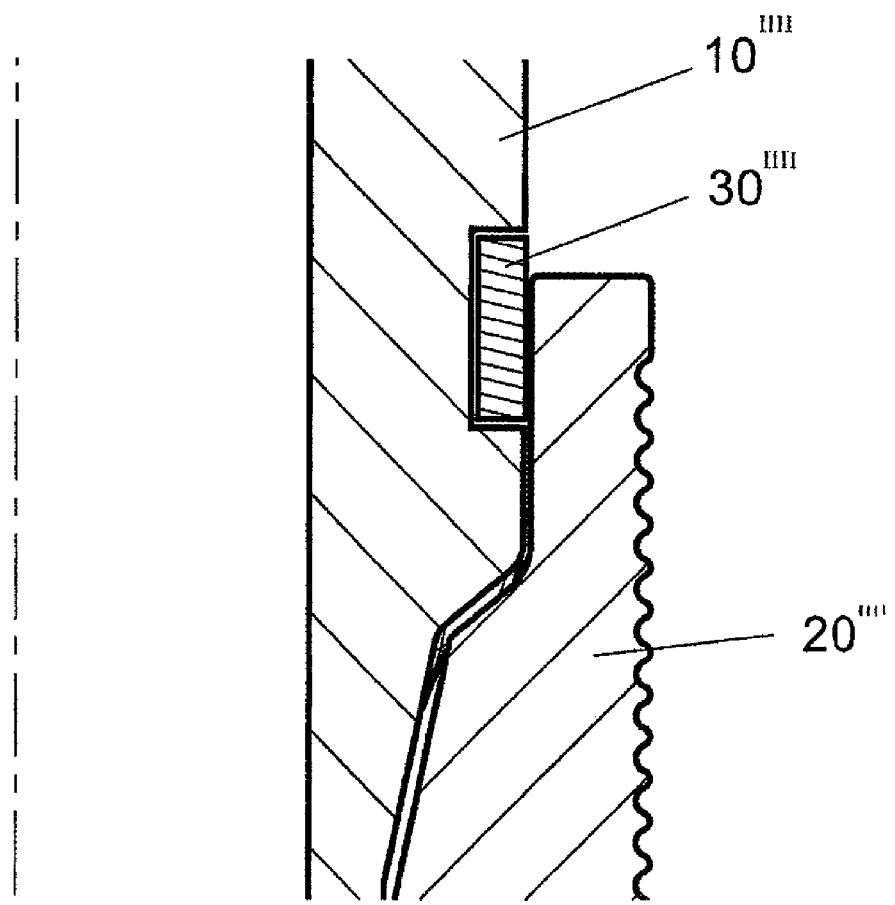
FIG. 29 shows an alternative variant of a seal.
Figure 30:
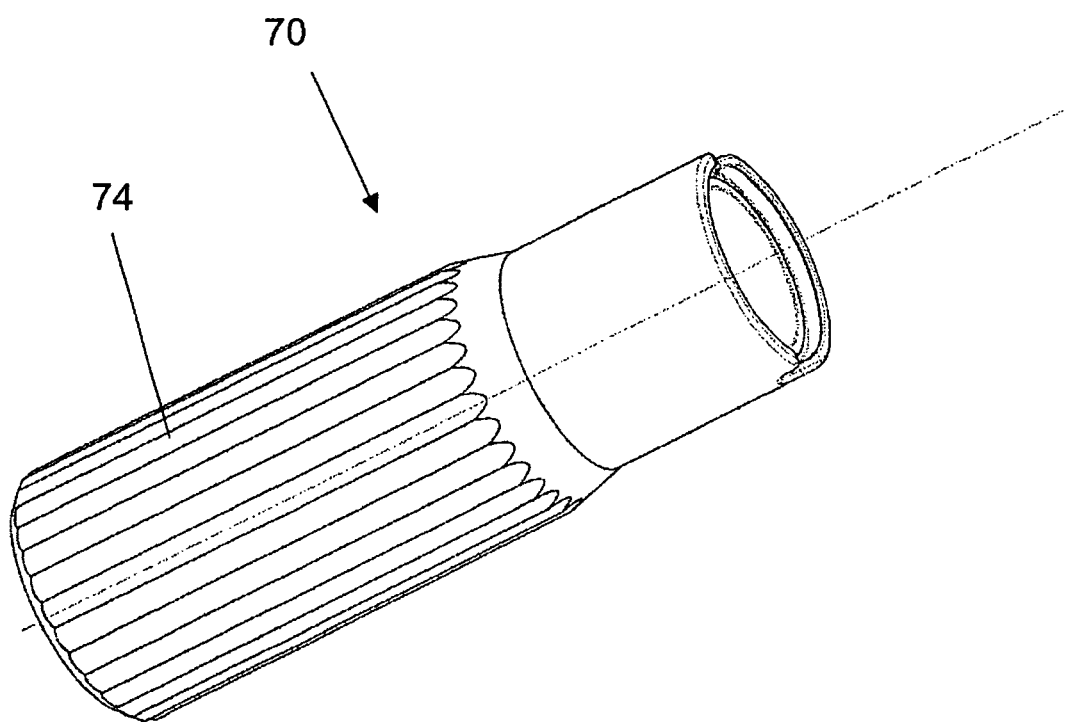
FIG. 30 shows a perspective view of a sealing body carrier.
Figure 31:
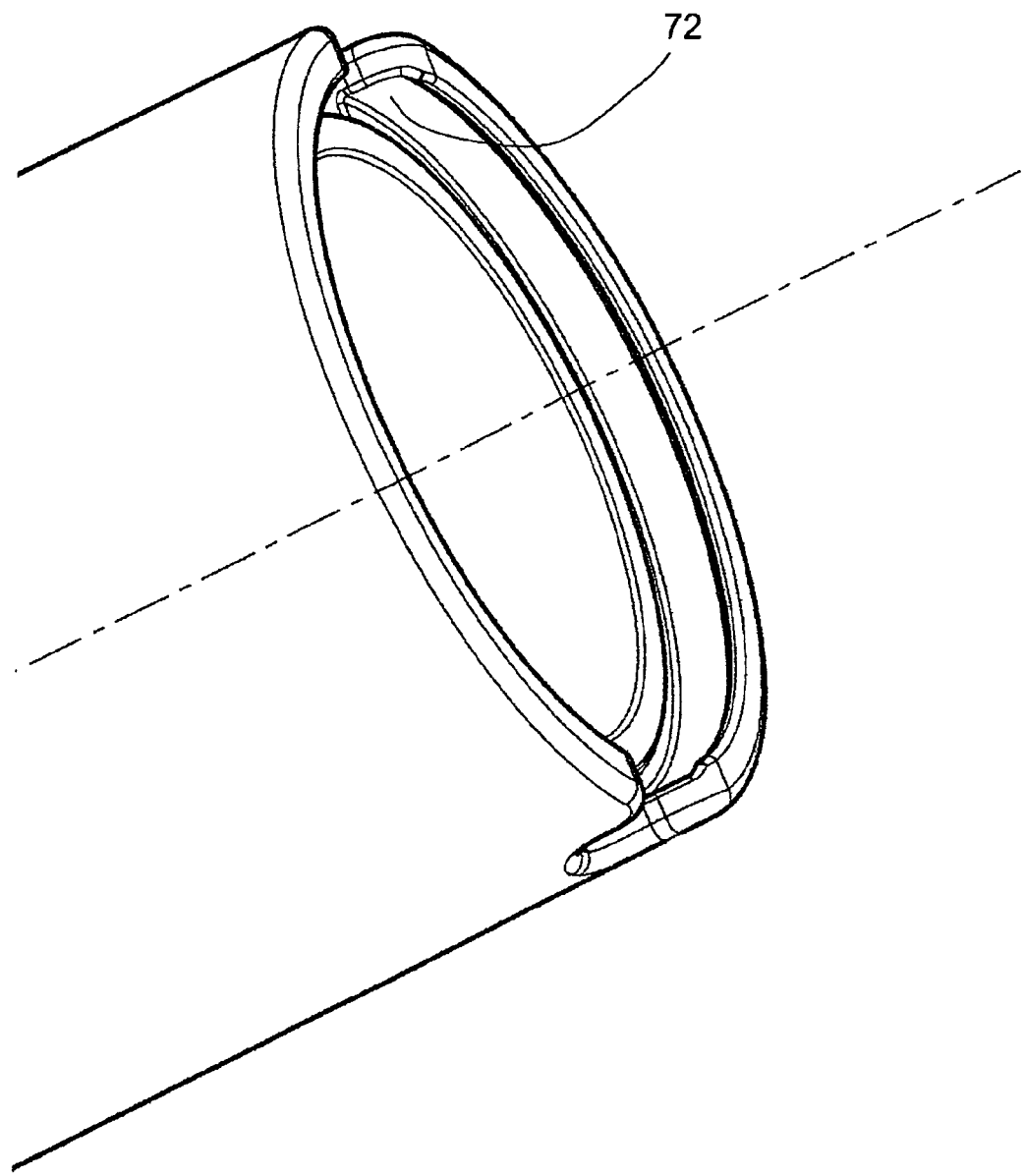
FIG. 31 shows an enlarged portion of the sealing body receiving means of the sealing body carrier in a perspective view as shown in FIG. 30.
Figure 32:
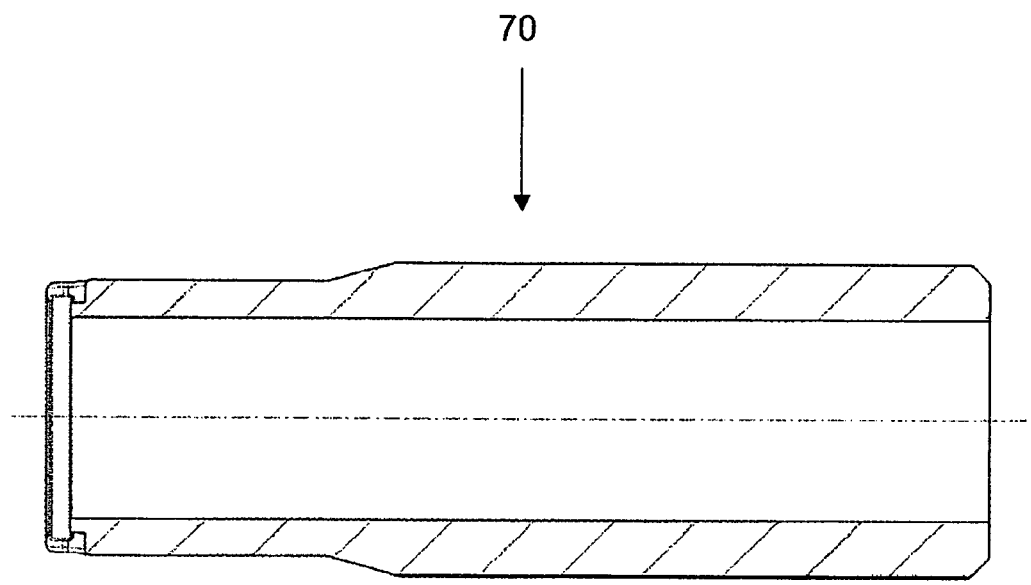
FIG. 32 shows a longitudinal section through the sealing body carrier of FIG. 30.
Figure 33:
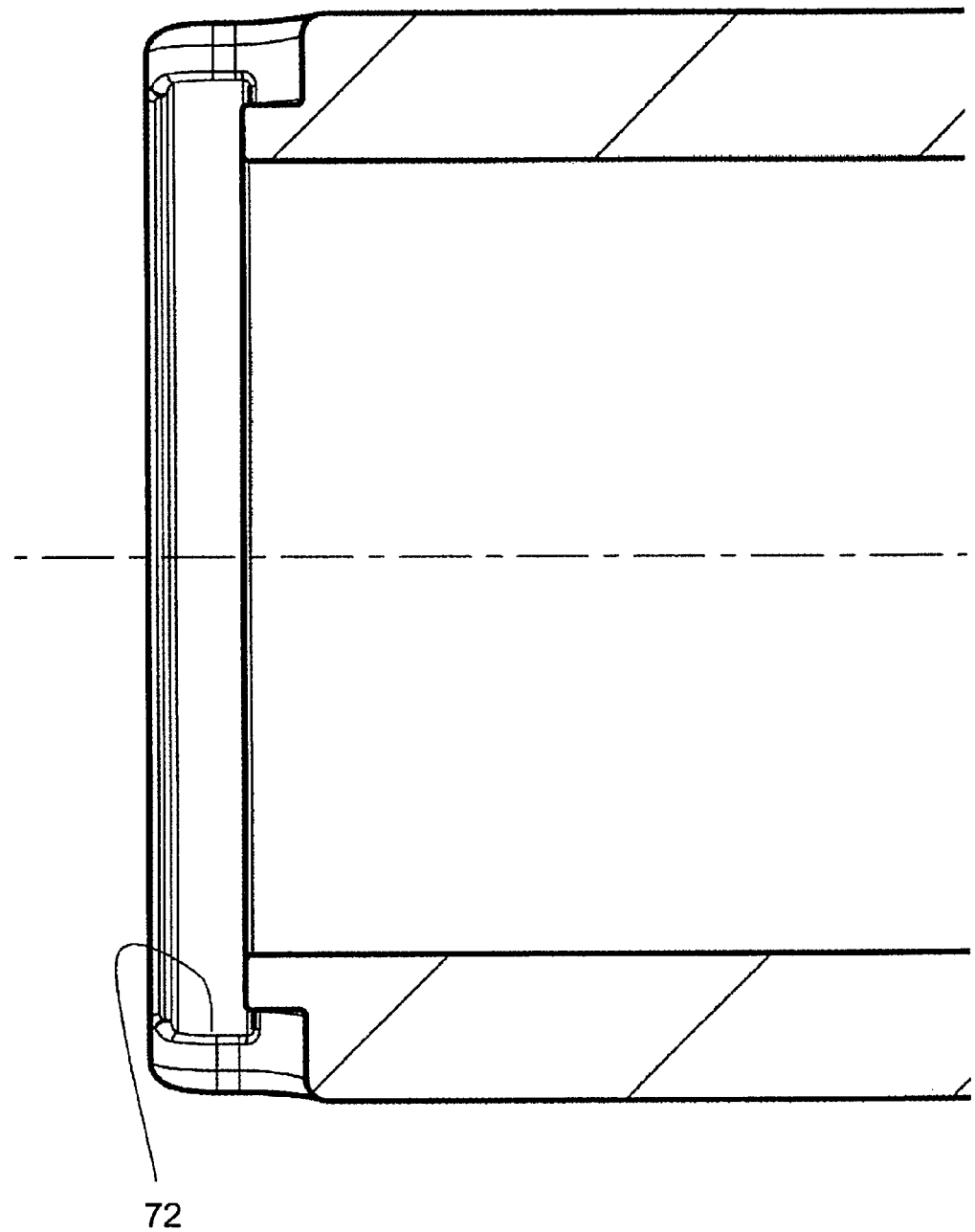
FIG. 33 shows an enlarged portion of the sealing body receiving means of the sealing body carrier in longitudinal section as shown in FIG. 32.
Figure 34:
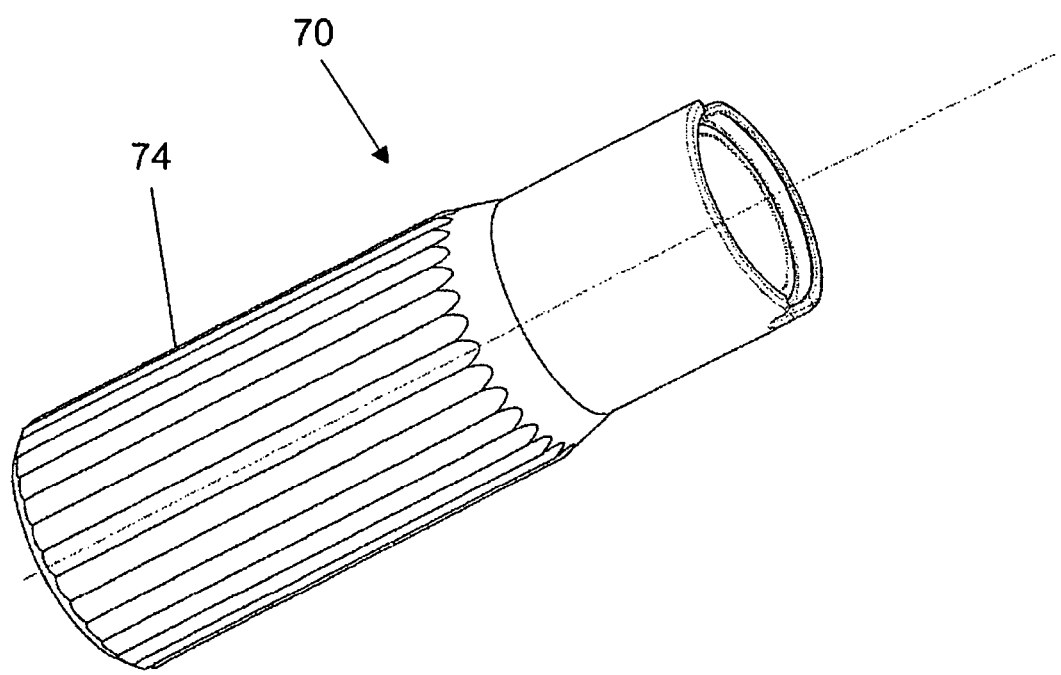
FIG. 34 shows a perspective view of the sealing body carrier with inserted sealing body.
Figure 35:
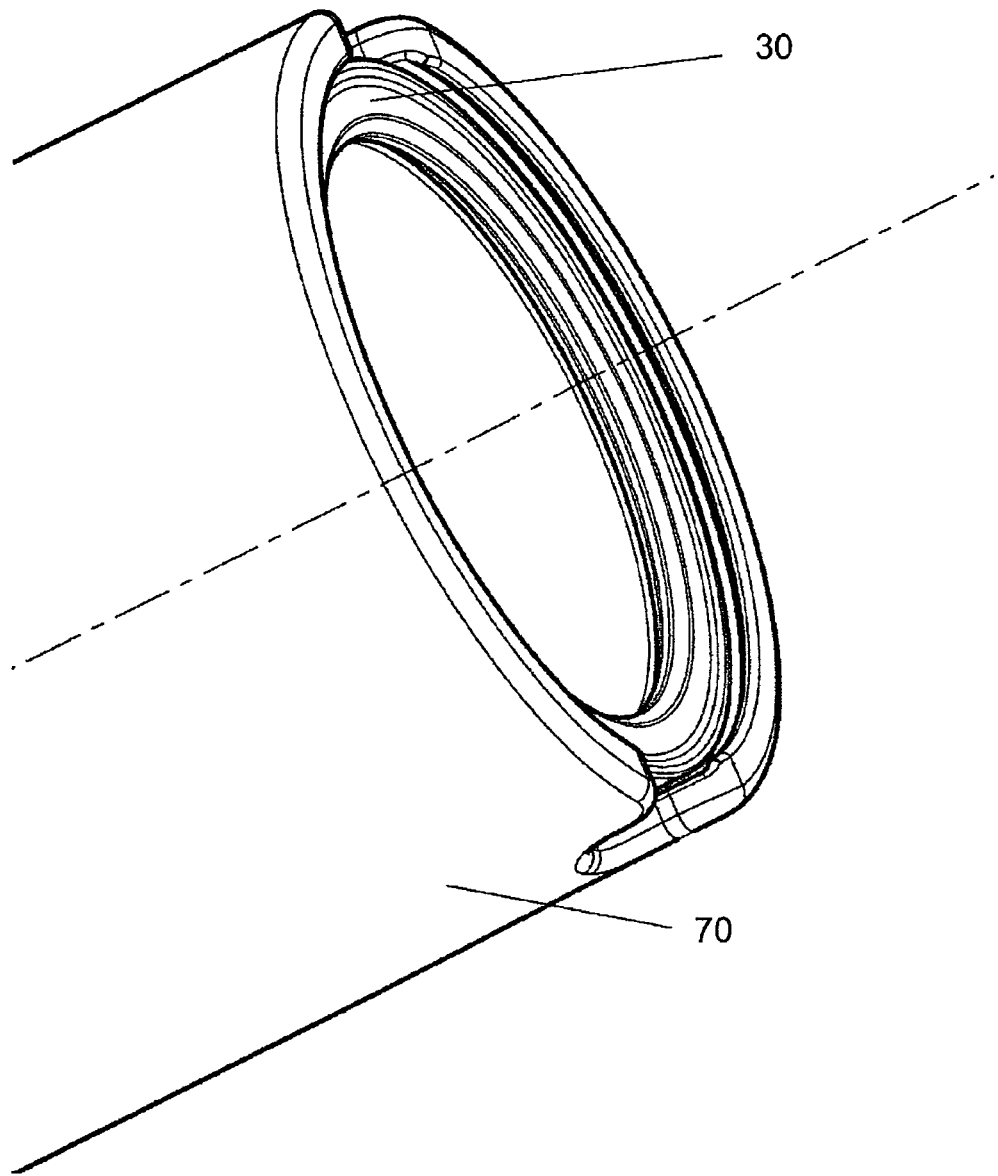
FIG. 35 shows an enlarged portion from the perspective view of the sealing body carrier with inserted sealing body in FIG. 34.
Figure 36:
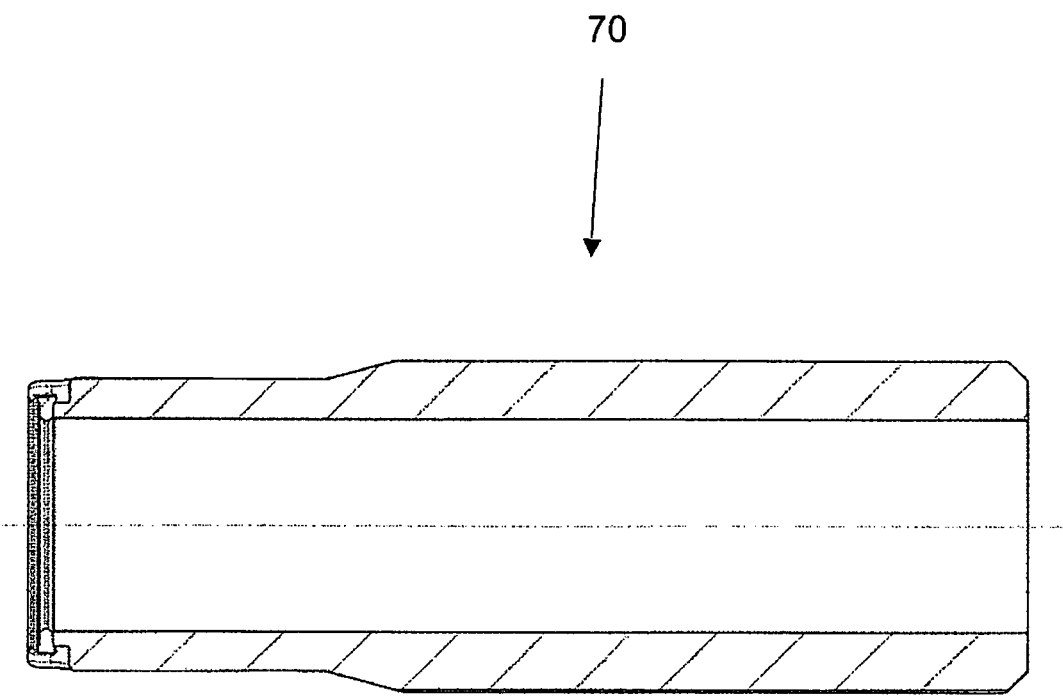
FIG. 36 shows a longitudinal section through the sealing body carrier with inserted sealing body as shown in FIG. 34.
Figure 37:
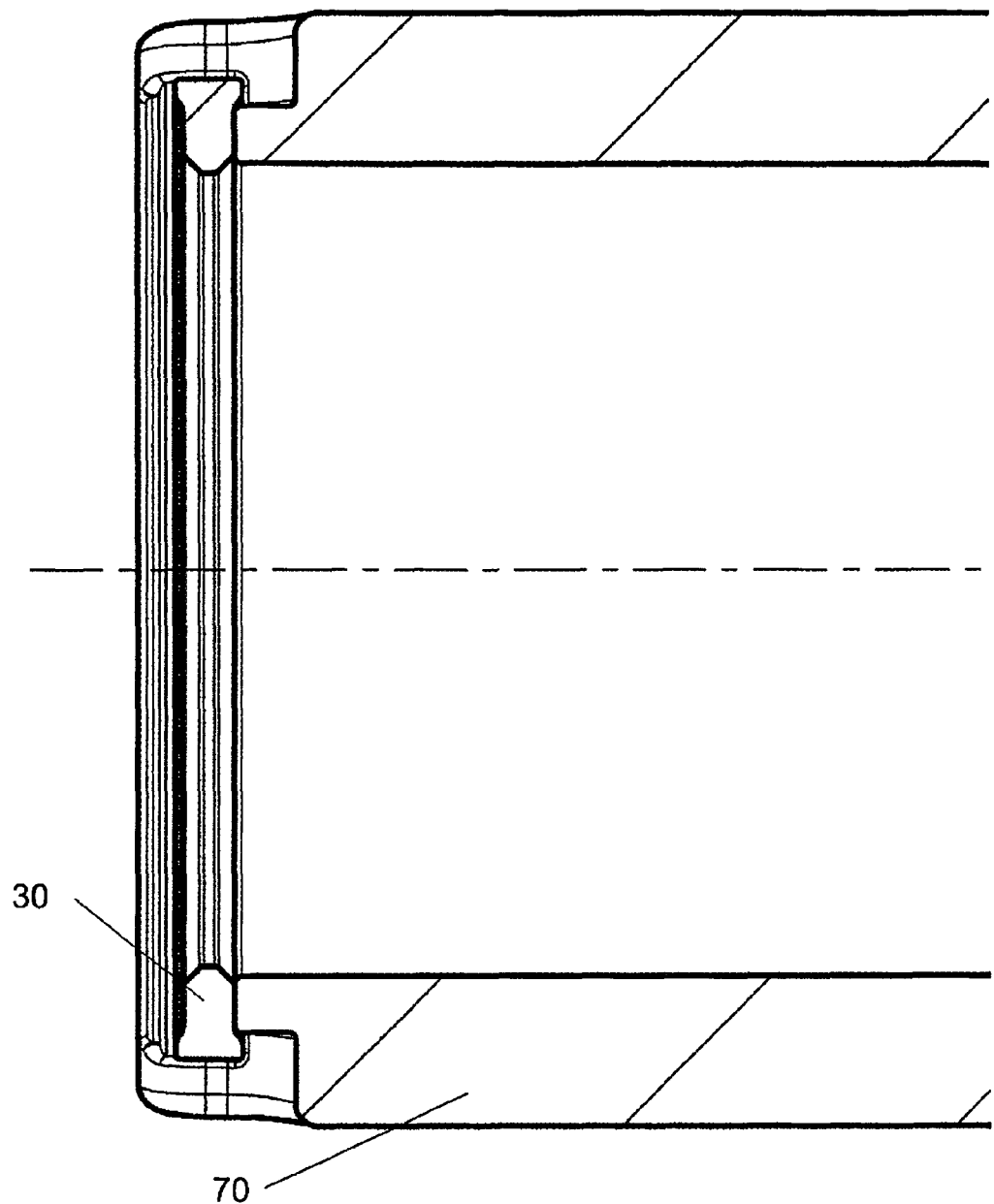
FIG. 37 shows an enlarged portion from the longitudinal section of the sealing body carrier with inserted sealing body as in FIG. 36.
Figure 38:
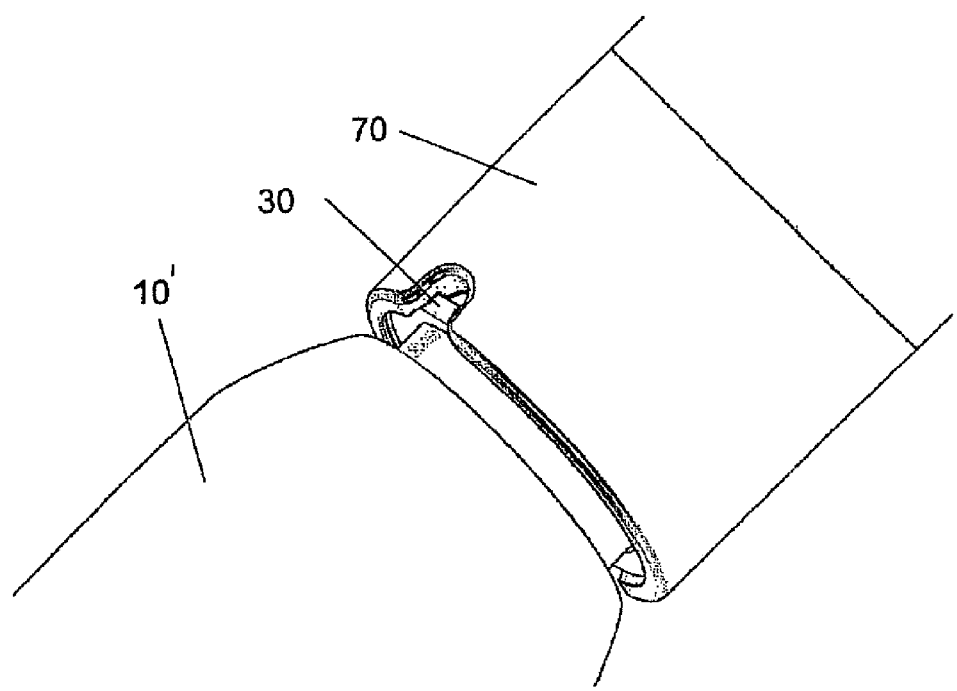
FIG. 38 shows the sealing body carrier of FIGS. 30 to 37 with inserted sealing body when fitting the sealing body on to the proximal stem portion.

FIG. 29 shows a seal having a sealing body 30'''' comprising an expandable material such as for example expandable metal or a plastic material with a high coefficient of thermal expansion. The sealing body 30'''' of FIG. 29 is in the form of a tube portion. The intermediate space between the proximal and the distal implant portions 10'''' and 20'''' respectively is of a corresponding configuration.

FIGS. 30 to 38 show a sealing body carrier 70 which serves as a tool for fitting a sealing body 30 on the proximal stem portion 10. At one end the sealing body carrier 70 has an inwardly open groove 72, into which a sealing body 30 can be inserted. Preferably the sealing body carrier 70 is fitted with the sealing body directly after manufacture of the sealing body 30 by the manufacturer thereof. That facilitates handling by the physician and improves hygiene. An externally fluted gripping region 74 facilitates handling in that respect.

The invention claimed is:

1. A dental implant comprising:
    a two part stem having a separate distal stem portion adapted for implantation in a jawbone and a separate proximal stem portion adapted to receive an artificial tooth structure, the distal stem portion having a longitudinal opening which is open towards a proximal end of the distal stem portion and has a curved inside wall, the inside wall defines V-shaped recesses which are open towards the proximal end of the distal stem portion, a distal end of the proximal stem portion having a curved outside wall which fits into the longitudinal opening of the distal stem portion, the distal and proximal stem portions in an interconnected condition at least indirectly adjoin each other at a connecting location and have mutually facing surfaces in the connecting location, the mutually facing surfaces extend transversely with respect to a longitudinal axis of the dental implant, the distal and proximal stem portions have abutment surfaces which bear against each other in the interconnected condition and which limit the degree of approach of the mutually facing surfaces of the stem portions so that the abutment surfaces define a minimum spacing of the mutually facing surfaces of the stem portions; and
    a sealing body provided between the mutually facing surfaces of the distal and proximal stem portions at the connecting location, the sealing body having sealing surfaces which face towards the mutually facing surfaces and which in the interconnected condition of the distal and proximal stem portions bear sealingly against the mutually facing surfaces thereof, the sealing body bridges over the minimum spacing of the mutually facing surfaces of the stem portions; and
    wherein the outside wall of the proximal stem portion in a of the distal end thereof has V-shaped projections which are matched to the V-shaped recesses of the distal stem portion in such a way that when the distal stem portion and the proximal stem portion are connected together, the V-shaped recesses and the V-shaped projections cooperate in mutual contact and form the abutment surfaces, and wherein each of the V-shaped recesses includes at least one flank surface facing inclined toward the proximal end of the distal stem portion.

2. A dental implant according to claim 1, wherein the inside wall of the proximal end of the distal stem portion and the outside wall of the distal end of the proximal stem portion are of a conical shape, and are arranged concentrically relative to each other and relative to a longitudinal axis of the dental implant.

3. A dental implant according to claim 1, wherein the sealing body comprises a circular disc with a central opening therethrough.

4. A dental implant according to claim 1, wherein the sealing body has concavely shaped end faces so that the thickness of the sealing body, measured in the longitudinal direction of the implant, is greater at least in a relaxed condition at a peripheral edge of the sealing body than in a central region of the sealing body.

5. A dental implant according to claim 1, wherein the sealing body is at least partially comprised of an elastic material.

6. A dental implant according to claim 5, wherein the elastic material of the sealing body is elastically compressible by at least 5% of a dimension in which it extends.

7. A dental implant according to claim 5, wherein the elastic material of the sealing body comprises a plastic material.

8. A dental implant according to claim 7, wherein the plastic material comprises an elastomer, a thermoplastic material, or a duromer blend.

9. A dental implant according to claim 8, wherein the plastic material has a coefficient of thermal expansion of more than $75 \times 10^{-6}$/K at 20° C.

10. A dental implant according to claim 7 wherein the sealing body further comprises at least one metal constituent or at least one ceramic constituent.

11. A dental implant according to claim 1, wherein at least one outside surface of the sealing body, that forms an outside surface of the implant, is coated with a layer, wherein the layer comprises metal, ceramic or plastic, and wherein the layer prevents ingress of bacteria into constituent parts of the sealing body which are covered by the layer.

12. A dental implant according to claim 11, wherein the layer comprises metal including at least one of titanium, silver and gold.

13. A dental implant according to claim 11, wherein the layer comprises plastic including PTFE.

14. A dental implant according to claim 1, wherein at least the sealing surfaces of the sealing body comprise an elastic, biocompatible, mouth-resistant, sterilizable plastic material.

15. A dental implant according to claim 1, wherein the sealing body is arranged in a radial free space between the mutually facing surfaces of the distal and proximal stem portions, wherein the extent of the sealing body in a radial direction is greater than the free space between the distal and the proximal stem portions in the interconnected condition thereof.

16. A dental implant according to claim 1, wherein the distal stem portion has four of the V-shaped recesses which are distributed uniformly over the periphery of the inside wall and the proximal stem portion correspondingly has four of the V-shaped projections which are also distributed uniformly over the periphery of the outside wall.

17. A dental implant according to claim 1, wherein the outside wall of the proximal stem portion is generally conical in a region of the V-shaped projections.

18. A dental implant according to claim 17, wherein the inside wall of the longitudinal opening of the distal stem portion is conical in a region of the V-shaped recesses.

19. A dental implant according to claim 1, wherein the sealing body is of such dimensions that it is compressed in an axial direction of the stem when the distal stem portion and the proximal stem portion have assumed their definitive axial relative position with respect to each other.

20. A dental implant according to claim 19, wherein the sealing body comprises circular sealing ring of rectangular material cross-section.

21. A dental implant according to claim 19, wherein the sealing body comprises a biocompatible plastic material.

22. A dental implant according to claim 1, wherein at least one of the distal stem portion and the proximal stem portion comprises biocompatible material.

23. A dental implant according to claim 22, wherein the biocompatible material comprises titanium or a titanium-bearing alloy.

24. A dental implant according to claim 1, wherein at least one of the distal stem portion and the proximal stem portion comprises ceramic.

25. A dental implant according to claim 24, wherein the ceramic comprises $ZrO_2$, $ZrO_2/Al_2O_3/Y_2O_3$ (ATZ), $ZrO_2/Y_2O_3$ (TZP) or $ZrO_2/Y_2O_3/Al_2O_3$ (TZP-A).

26. A dental implant according to claim 1, wherein at least one of the distal stem portion and the proximal stem portion comprises plastic material.

27. A dental implant according to claim 1, wherein the sealing body has an outer peripheral surface which forms an outer surface of the dental implant when assembled.

28. A dental implant according to claim 1, wherein the mutually facing surfaces extend parallel to each other.

* * * * *